(12) United States Patent
Li et al.

(10) Patent No.: US 6,703,393 B2
(45) Date of Patent: Mar. 9, 2004

(54) (OXO-PYRAZOLO[1,5A]PYRIMIDIN-2-YL) ALKYL-CARBOXAMIDES

(75) Inventors: Guiying Li, Branford, CT (US); John Peterson, Durham, CT (US); Pamela Albaugh, Carmel, IN (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 10/107,790

(22) Filed: Mar. 27, 2002

(65) Prior Publication Data

US 2003/0109536 A1 Jun. 12, 2003

Related U.S. Application Data

(60) Provisional application No. 60/279,147, filed on Mar. 27, 2001.

(51) Int. Cl.[7] .................... C07D 487/04; C07D 471/04; A61P 25/22; A61P 25/24; A61P 25/28
(52) U.S. Cl. .................... 514/259.3; 206/568; 514/267; 544/250; 544/281
(58) Field of Search ................. 544/250, 281; 514/267, 259.3; 206/568

(56) References Cited

U.S. PATENT DOCUMENTS

| | | | |
|---|---|---|---|
| 4,950,585 A * | 8/1990 | Tachibana et al. .......... 430/385 |
| 5,723,608 A | 3/1998 | Yuan | |
| 6,271,241 B1 | 8/2001 | DeSimone et al. | |
| 6,358,949 B1 | 3/2002 | DeSimone et al. | |
| 6,380,210 B1 | 4/2002 | DeSimone et al. | |
| 6,420,365 B1 | 7/2002 | Peterson et al. | |
| 6,552,037 B2 | 4/2003 | Cai et al. | |
| 2002/0035120 A1 | 3/2002 | Cai et al. | |
| 2002/0055524 A1 | 5/2002 | Maynard et al. | |
| 2002/0128236 A1 | 9/2002 | Maynard et al. | |
| 2003/0176450 A1 * | 9/2003 | Atkinson et al. ........ 514/259.3 |

FOREIGN PATENT DOCUMENTS

| | | |
|---|---|---|
| EP | 0 591 528 | 4/1994 |
| EP | 0 795 555 | 9/1997 |
| GB | 2 157 285 | 10/1985 |

* cited by examiner

*Primary Examiner*—Mark L. Berch
(74) *Attorney, Agent, or Firm*—McDonnell Boehnen Hulbert & Berghoff

(57) ABSTRACT

Disclosed are compounds of the formula

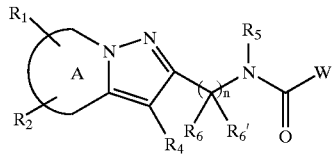

and the pharmaceutically acceptable salts thereof where the variables $R_1$, $R_2$, A, $R_4$, $R_5$, $R_6$, $R_6'$, n, and W are defined herein. These compounds bind to the benzodiazepine site of $GABA_A$ receptors are provided and, therefore can be used to modulate ligand binding to $GABA_A$ receptors in vivo or in vitro, and are particularly useful in the treatment of a variety of central nervous system (CNS) disorders in humans, domesticated companion animals and livestock animals.

68 Claims, No Drawings

(OXO-PYRAZOLO[1,5A]PYRIMIDIN-2-YL) ALKYL-CARBOXAMIDES

BACKGROUND OF THE INVENTION

This application claims priority from U.S. Provisional Application Ser. No. 60/279,147, filed Mar. 27, 2001, the disclosure of which is hereby incorporated by reference in its entirety.

1. Field of the Invention

This invention relates to (oxo-pyrazolo[1,5a]pyrimidin-2-yl)alkyl-carboxamides that bind and more specifically to such components to the benzodiazepine site of $GABA_A$ receptors. This invention also relates to pharmaceutical compositions comprising such compounds and to the use of such compounds in the treatment of central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the $GABA_A$ receptor, which causes alteration in chloride conductance and membrane polarization. In addition to being the site of neurotransmitter action, a number of drugs including the anxiolytic and sedating benzodiazepines bind to this receptor. The $GABA_A$ receptor comprises a chloride channel that generally, but not invariably, opens in response to GABA, allowing chloride to enter the cell. This, in turn, effects a slowing of neuronal activity through hyperpolarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native $GABA_A$ receptors are typically composed of 2α, 2β, and 1γ subunits (Pritchett & Seeburg *Science* 1989; 245:1389–1392, and Knight et. al., *Recept. Channels* 1998; 6:1–18). Various lines of evidence (such as message distribution, genome localization and biochemical study results) suggest that the major naturally occurring receptor combinations are $α_1β_2γ_2$, $α_2β_3γ_2$, $α_3β_3γ_2$, and $α_5β_3γ_2$ (Mohler et al. *Neuroch. Res.* 1995; 20 (5):631-36).

The $GABA_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the $GABA_A$ receptor. In addition to the benzodiazepine site (sometimes referred to as the benzodiazepine or BDZ receptor), the $GABA_A$ receptor contains sites of interaction for several other classes of drugs. These include a steroid binding site, a picrotoxin site, and a barbiturate site. The benzodiazepine site of the $GABA_A$ receptor is a distinct site on the receptor complex that does not overlap with the site of interaction for other classes of drugs that bind to the receptor or for GABA (see, e.g., Cooper, et al., The Biochemical Basis of Neuropharmacology, $6^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open $GABA_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as $GABA_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

The invention provides (oxo-pyrazolo[1,5a]pyrimidin-2-yl)alkyl-carboxamides and specifically to such compounds that interact with the benzodiazepine site of $GABA_A$ receptors, including human $GABA_A$ receptors. Preferred compounds of the invention interact with high selectivity and/or high affinity to $GABA_A$ receptors and act as agonists, antagonists or inverse agonists of such receptors. As such, they are useful in the treatment of a variety of CNS disorders.

In one aspect, the invention provides compounds of Formula I:

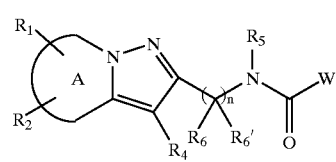

Formula I and pharmaceutically acceptable salts thereof, wherein:
n is 1, 2, or 3;

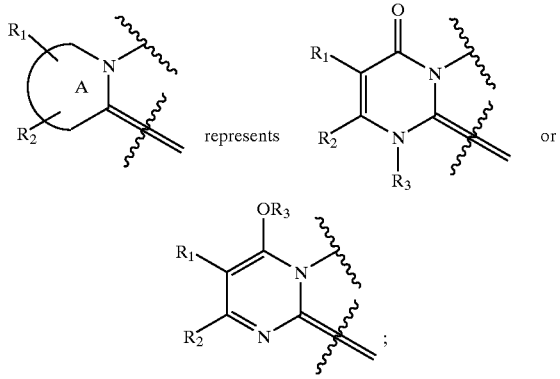

where $R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; or $R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy;

$R_3$, $R_4$ and $R_5$ are independently chosen from (i) hydrogen; and (ii) $C_1$–$C_6$ acyl and $C_1$–$C_6$ alkyl, each of which is optionally substituted with up to three substituents independently chosen from halogen, hydroxy, halo($C_1$–$C_2$)alkyl, halo($C_1$–$C_2$)alkoxy, methoxy, ethoxy, $C_3$–$C_7$ cycloalkyl, phenyl, pyridyl, and pyrimidyl, wherein each of phenyl, pyridyl, and pyrimidyl is optionally substituted with up to three groups selected independently from halogen, $C_1$–$C_6$ alkyl, $C_1$–$C_6$ alkoxy, hydroxy and amino;

$R_6$ and $R_6'$ are independently selected at each occurrence from hydrogen and $C_1$–$C_6$ alkyl;

W is aryl or heteroaryl (such as phenyl, naphthyl, pyridyl, pyrimidinyl, pyridizinyl, pyrrolyl, imidazolyl, pyrazolyl or thiophenyl), each of which is optionally substituted with up to 5 groups independently selected from hydrogen, halogen, hydroxy, amino, mono- or di($C_1$–$C_6$) alkyl amino, halo($C_1$–$C_6$)alkyl, halo($C_1$–$C_6$)alkoxy, $C_1$–$C_6$ alkyl, and $C_1$–$C_6$ alkoxy.

In another aspect, the invention provides compounds of formula Ia:

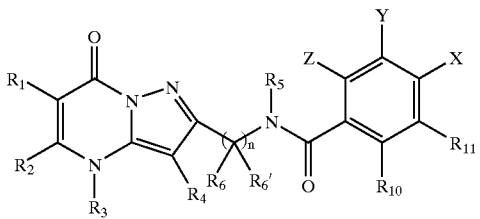

and pharmaceutically acceptable salts thereof, wherein:
n is 1, 2, or 3;
$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy; or $R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy;

$R_3$, $R_4$ and $R_5$ are independently chosen from (i) hydrogen; and (ii) $C_1$–$C_6$ acyl and $C_1$–$C_6$ alkyl, each of which is optionally substituted with up to three substituents independently chosen from halogen, hydroxy, halo($C_1$–$C_2$) alkyl, halo($C_1$–$C_2$)alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;

$R_6$ and $R_6'$ are independently selected at each occurrence from hydrogen and $C_1$–$C_6$ alkyl; and $R_{10}$, $R_{11}$, X, Y and Z are independently selected from hydrogen, halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy.

In yet another aspect, the invention provides compounds of formula Ib:

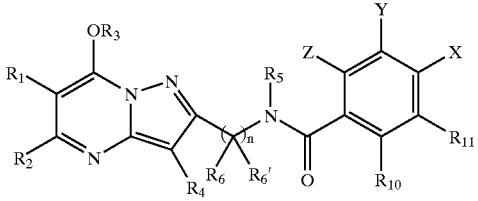

and pharmaceutically acceptable salts thereof, wherein:
n is 1, 2, or 3;
$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy, or $R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy;

$R_3$, $R_4$ and $R_5$ are independently chosen from (i) hydrogen; and (ii) $C_1$–$C_6$ acyl and $C_1$–$C_6$ alkyl, each of which is optionally substituted with up to three substituents independently chosen from halogen, hydroxy, halo($C_1$–$C_2$)alkyl, halo ($C_1$–$C_2$)alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;

$R_6$ and $R_6'$ are independently selected at each occurrence from hydrogen and $C_1$–$C_6$ alkyl; and $R_{10}$, $R_{11}$, X, Y and Z are independently selected from hydrogen, halogen, hydroxy, amino, mono- and di($C_1$–$C_6$)alkyl amino, halo ($C_1$–$C_6$)alkyl, halo($C_1$–$C_6$)alkoxy, $C_1$–$C_6$ alkyl and $C_1$–$C_6$ alkoxy.

The invention also provides pharmaceutical compositions comprising a compound or pharmaceutically acceptable salt of Formulas I, Ia, or Ib, and at least one pharmaceutically acceptable carrier, or excipient.

The invention also provides methods for the treatment of anxiety, depression, a sleep disorder, attention deficit disorder, or Alzheimer's dementia, comprising administering to a patient in need of such treatment a therapeutically effective amount of a compound of Formulas I, Ia, or Ib.

The invention further provides methods for potentiating a therapeutic effect of a CNS agent, comprising administering to a patient a CNS agent and a compound of Formulas I, Ia, or Ib.

The invention further provides methods for determining the presence or absence of $GABA_A$ receptor in a sample, comprising:

(a) contacting a sample with a compound of any one of Formula I, Ia, and Ib under conditions that permit binding of the compound to $GABA_A$ receptor; and (b) detecting a level of compound bound to $GABA_A$ receptor, and therefrom determining the presence or absence of $GABA_A$ receptor in the sample.

In another aspect, the invention provides methods for making the compounds of Formula I. And, in a related aspect, the invention provides intermediate compounds for use in methods for preparing compounds of Formula I.

The invention further provides methods for altering the signal-transducing activity of at least one $GABA_A$ receptor, comprising contacting a cell expressing $GABA_A$ receptor(s) with a compound of Formula I in an amount sufficient to detectably alter the electrophysiology of the cell, and thereby altering $GABA_A$ receptor signal-transducing activity.

DETAILED DESCRIPTION OF THE INVENTION

Definitions

Prior to setting forth the invention in detail, it may be helpful to provide definitions of certain terms to be used herein. Compounds of the present invention are generally described using standard nomenclature. For compounds having asymmetric centers, it should be understood that all of the optical isomers and mixtures thereof are encompassed. In addition, compounds with carbon—carbon double bonds may occur in Z- and E- forms, with all isomeric forms of the compounds being included in the present invention. Where a compound exists in various tautomeric forms, the invention is not limited to any one of the specific tautomers, but rather includes all tautomeric forms.

Certain compounds are described herein using a general formula that includes variables. Unless otherwise specified, each variable within such a formula is defined independently of other variable, and any variable that occurs more than one time within a formula is defined independently at each occurrence. Thus, for example, if a group is described as being substituted with 0–2 R, then the group may be unsubstituted or substituted with up to two R groups and R at each occurrence is selected independently from the definition of R. In addition, it will be apparent that combinations of substituents and/or variables are permissible only if such combinations result in stable compounds.

As used herein, "alkyl" refers to branched and straight-chain hydrocarbon groups. Preferred alkyl groups are $C_1$–$C_6$ alkyl (i.e., alkyl groups having from 1 to 6 carbon atoms). Alkyl groups of 2 or more carbon atoms may contain double or triple bonds, which may occur at any stable point along the chain (e.g., ethynyl and propargyl). A "stable point" is bond that, when unsaturated, results in a chemically stable compound (i.e., a compound that can be isolated, characterized and tested for biological activity). Examples of alkyl groups include, but are not limited to, methyl, ethyl, n-propyl, i-propyl, n-butyl, s-butyl, t-butyl, n-pentyl and s-pentyl. An alkyl group may be bonded to an atom within a molecule of interest via any chemically suitable portion of the alkyl group.

As used herein, "alkoxy" represents an alkyl group as defined above attached via an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy and 3-methylpentoxy. "$C_1$–$C_6$ alkoxy" indicates alkoxy groups having from 1 to 6 carbon atoms.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred aryl groups include phenyl, naphthyl, including 1-naphthyl and 2-naphthyl, and acenaphthyl. More preferred aryl groups include phenyl and napthyl. The aryl groups herein are unsubstituted or, as specified, substituted in one or more substitutable positions with various groups. Thus, such aryl groups can be optionally substituted with, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di(($C_1$–$C_6$)alkylamino($C_1$–$C_6$)alkyl.

The term "halogen" includes fluorine, chlorine, bromine, and iodine.

As used herein, "haloalkyl" refers to alkyl groups (preferably saturated aliphatic hydrocarbon groups) that are substituted with 1 or more halogen (for example-$C_vF_w$, where v is an integer of from 1 to 3 and w is an integer of from 1 to (2v+1). Examples of haloalkyl groups include, but are not limited to, mono-, di- or tri-fluoromethyl; mono-, di- or tri- chloromethyl; mono-, di-, tri-, tetra- or penta-fluoroethyl; and mono-, di-, tri-, tetra- or penta-chloroethyl. "Halo($C_1$–$C_6$)alkyl" groups have 1 to 6 carbon atoms.

The term "haloalkoxy" refers to a haloalkyl group as defined above attached via an oxygen bridge. "Halo($C_1$–$C_6$) alkoxy" groups have 1 to 6 carbon atoms. Examples of haloalkoxy groups include, but are not limited to, trifluoromethoxy and trichloromethoxy.

As used herein, the term "heteroaryl" means stable monocyclic, bicylclic and tricyclic ring systems which contain at least one aromatic ring where the aromatic ring contains from 5–7 members and from 1 to 4 hetero atoms independently selected from the group consisting of nitrogen, oxygen, and sulfur; the remaining rings contain from 5–7 members selected from carbon, oxygen, nitrogen, and sulfur. The aromatic ring containing a hetero atom is the "heteroaromatic ring." In bicyclic and tricyclic ring systems, the heteroaromatic ring may be fused to a carbocyclic ring that may be aromatic, such as benzo, or to a heteroaromatic ring, such as pyrido or pyrrolidino, or to heteroaromatic and one carbocyclic ring. Thus, "heteroaryl" includes ring systems having from one to three rings of from 5–7 ring members in each ring and where at least one ring is aromatic and contains from one to four hetero atoms. Any of the rings in the heteroaryl groups may be further fused to another ring forming a spiro ring system.

The nitrogen and sulfur heteroatoms may optionally be oxidized. The heterocyclic ring may be attached to its pendant group at any heteroatom or carbon atom which results in a stable structure. The heterocyclic rings described herein may be substituted on any substitutable carbon or nitrogen atom that results in a stable compound. Examples of suitable heteraryl substituents are $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, and mono- or di($C_1$–$C_6$)alkylamino($C_1$–$C_6$)alkyl.

Examples of heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, quinazolinyl, quinolinyl, 4H-quinolizinyl, quinoxalinyl, quinuclidinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heteroaryl groups include, but are not limited to, pyridyl, pyrimidinyl, pyridizinyl, pyrrolyl, imidazolyl, pyrazolyl and thiophenyl.

By "$C_1$–$C_6$ acyl" herein is meant groups of the formula $R_cC(0)$— where $R_c$ is alkyl of 1–5 carbon atoms.

A "carbocyclic ring" is a ring formed entirely by carbon—carbon bonds. Unless otherwise specified, such a ring may be aromatic or non-aromatic (unsaturated, partially saturated or saturated), and is optionally substituted. Typically, each ring contains from 3 to 8 (preferably from 5 to 7) ring members. If a ring contains one or more substitutions, each substitution is selected independently of any other substitutions. Where $R_1$ and $R_2$ (together with the atoms to which they are attached) form a partially saturated or unsaturated carbocyclic ring of from 4 to 8 carbon atoms, it is understood that the carbocyclic rings contain at least one double bond or contain sufficient double bonds to form an aromatic carbocyclic ring. Representative examples of ring systems resulting from $R_1$ and $R_2$ forming such a partially saturated or unsaturated carbocyclic ring (which is fused to the pyrazolopyrimidine group include, but are not limited to, the following structures:

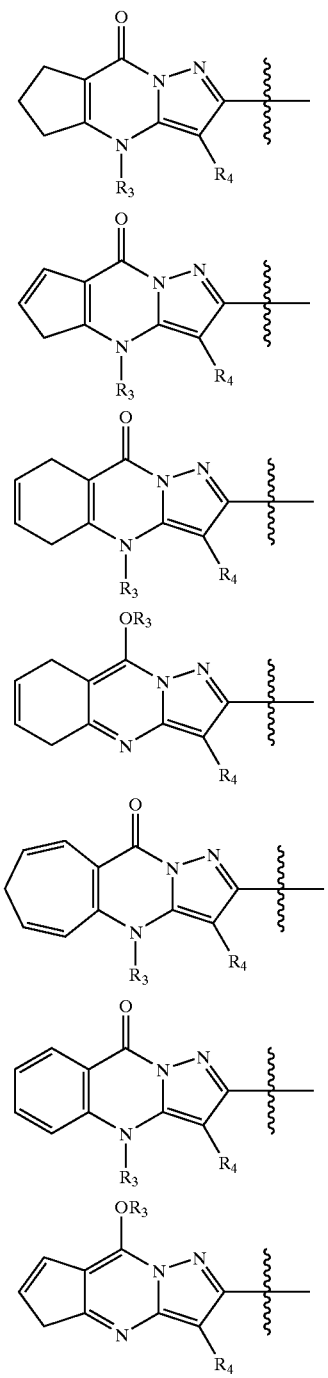

-continued

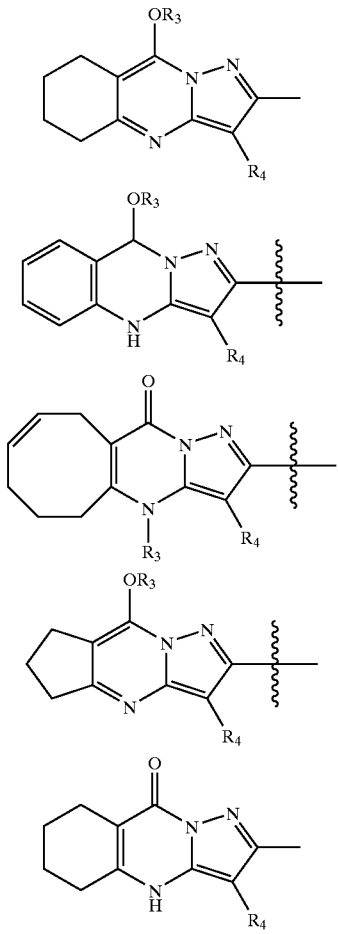

A "substituent," as used herein, refers to a molecular moiety that is covalently bonded to an atom within a molecule of interest. For example, a "ring substituent" may be a moiety such as a halogen, alkyl group, alkoxy group, haloalkyl group or other group as discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

A dash ("-") that is not between two letters or symbols is used to indicate a point of attachment for a substituent. For example, —CONH$_2$ is attached through the carbon atom.

The term "GABA$_A$ receptor" refers to a protein complex that detectably binds GABA and mediates a dose dependent alteration in chloride conductance and membrane polarization. Receptors comprising naturally-occurring mammalian (especially human or rat) GABA$_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate GABA$_A$ receptor for GABA may be evaluated using a standard ligand binding assay as provided herein. It will be apparent that there are a variety of GABA$_A$ receptor subtypes that fall within the scope of the term "GABA$_A$ receptor." These subtypes include, but are not limited to, $\alpha_2\beta_3\gamma_2$, $\alpha_3\beta_3\gamma_2$, and $\alpha_1\beta_2\gamma_2$ receptor subtypes. GABA$_A$ receptors may be obtained from a variety of sources, such as from preparations of rat cortex or from cells expressing cloned human GABA$_A$ receptors.

A "prodrug" is a compound that does not fully satisfy the structural requirements of the compounds provided herein, but is modified in vivo, following administration to a patient, to produce an active compound of the present invention. For example, a prodrug may be an ester or an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "patient" is any individual treated with a compound provided herein. Patients include humans, as well as other animals such as companion animals and livestock. Patients may be afflicted with a CNS disorder, or may be free of such a condition (i.e., treatment may be prophylactic).

A "CNS disorder" is a disease or condition of the central nervous system that is responsive to GABA$_A$ receptor modulation in the patient. Such disorders include anxiety disorders (e.g., panic disorder, obsessive compulsive disorder, agoraphobia, social phobia, specific phobia, dysthymia, adjustment disorders, separation anxiety, cyclothymia, and generalized anxiety disorder), stress disorders (e.g., post-traumatic stress disorder, anticipatory anxiety acute stress disorder and acute stress disorder), depressive disorders (e.g., depression, atypical depression, bipolar disorder and depressed phase of bipolar disorder), sleep disorders (e.g., primary insomnia, circadian rhythm sleep disorder, dyssomnia NOS, parasomnias including nightmare disorder, sleep terror disorder, sleep disorders secondary to depression, anxiety and/or other mental disorders and substance-induced sleep disorder), cognitive disorders (e.g., cognition impairment, mild cognitive impairment (MCI), age-related cognitive decline (ARCD), traumatic brain injury, Down Syndrome, neurodegenerative diseases such as Alzheimer's disease and Parkinson's disease, and stroke), AIDS-associated dementia, dementia associated with depression, anxiety or psychosis, attention deficit disorders (e.g., attention deficit disorder and attention deficit and hyperactivity disorder), convulsive disorders (e.g., epilepsy), benzodiazepine overdose and drug and alcohol addiction.

A "CNS agent" is any drug used to treat or prevent a CNS disorder. CNS agents include, for example: serotonin receptor (e.g., 5-HT$_{1A}$) agonists and antagonists and selective serotonin reuptake inhibitors (SSRIs); neurokinin receptor antagonists; corticotropin releasing factor receptor (CRF$_1$) antagonists; melatonin receptor agonists; nicotinic agonists; muscarinic agents; acetylcholinesterase inhibitors and dopamine receptor agonists.

A compound is said to have "high affinity" if the K$_i$ at a GABA$_A$ receptor is less than 1 micromolar, preferably less than 100 nanomolar or less than 10 nanomolar. A representative assay for determining $K_i$ at $GABA_A$ receptor is provided in Example 5, herein. It will be apparent that the $K_i$ may depend upon the receptor subtype used in the assay. In other words, a high affinity compound may be "subtype-specific" (i.e., the $K_i$ is at least 10-fold greater for one subtype than for another subtype). Such compounds are said to have high affinity for $GABA_A$ receptor if the $K_i$ for at least one $GABA_A$ receptor subtype meets the above criteria.

A compound is said to have "high selectivity" if it binds to a $GABA_A$ receptor with a $K_i$ that is at least 10-fold lower, preferably at least 100-fold lower, than the $K_i$ for binding to other membrane-bound receptors. In particular, the compound should have a $K_i$ that is at least 10-fold greater at the following receptors than at a $GABA_A$ receptor: serotonin, dopamine, galanin, VR1, C5a, MCH, NPY, CRF, bradykinin, NK-1, NK-3 and tackykinin. Assays to determine the Ki at other receptors may be performed using standard binding assay protocols.

Preferred compounds of Formula I are those where

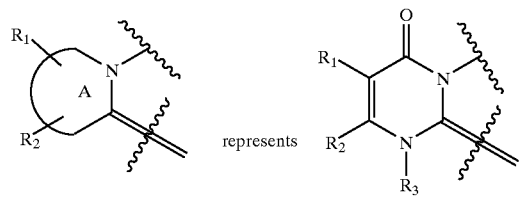

represents

In such preferred compounds, W is preferably heteroaryl optionally substituted with up to 5 groups independently selected from hydrogen, halogen, hydroxy, amino, mono- or di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy.

In other such preferred compounds, W is preferably phenyl optionally substituted with up to 5 groups independently selected from hydrogen, halogen, hydroxy, amino, mono- or di($C_1$–$C_6$)alkyl amino, halo($C_1$–$C_6$)alkyl, halo ($C_1$–$C_6$)alkoxy, $C_1$–$C_6$ alkyl, and $C_1$–$C_6$ alkoxy.

Even more preferred compounds of Formula I are those wherein:

W is pyridyl, pyrimidinyl, pyridizinyl, pyrrolyl, imidazolyl, pyrazolyl or thiophenyl, each of which is optionally substituted with up to 5 groups independently selected from hydrogen, halogen, hydroxy, amino, mono- or di($C_1$–$C_6$)alkyl amino, halo($C_1$–$C_6$)alkyl, halo($C_1$–$C_6$) alkoxy, $C_1$–$C_6$ alkyl, and $C_1$–$C_6$ alkoxy.

Particularly preferred compounds are those where W is phenyl, optionally substituted with 4, or more preferably 3, groups independently selected from halogen, hydroxy, amino, mono($C_1$–$C_6$)alkyl amino, di($C_1$–$C_6$)alkylamino, haloalkyl, $C_1$–$C_6$ alkyl, and $C_1$–$C_6$ alkoxy.

Yet even more preferred compounds of Formula I are those wherein:

$R_4$ and $R_5$ are independently $C_1$–$C_6$ alkyl optionally substituted with 1 or 2 substituents independently chosen from halogen, hydroxy, trifluoromethyl, trifluoromethoxy, methoxy, ethoxy, $C_3$–$C_7$ cycloalkyl, phenyl, pyridyl, and pyrimidyl, wherein each of phenyl, pyridyl, and pyrimidyl is optionally substituted with up to three groups independently selected from halogen, $C_1$–$C_6$ alkyl, $C_1$–$C_6$ alkoxy, hydroxy and amino.

More preferred compounds of Formula I are those wherein:

$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; and $R_3$, $R_4$ and $R_5$ are independently $C_1$–$C_6$ alkyl.

More preferred compounds of Formula I are those wherein:

$R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy; and $R_3$, $R_4$ and $R_5$ are independently H or $C_1$–$C_6$ alkyl.

Even more preferred compounds of Formula I are those wherein:

$R_1$ and $R_2$ together with the atoms with which they are attached form a cyclopentenyl, cyclopentadienyl, cyclohexenyl, cyclohexadienyl, cycloheptatrienyl, cycloheptadienyl, phenyl, cyclooctadienyl, and cyclooctenyl, wherein each ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; and $R_3$, $R_4$ and $R_5$ are independently $C_1$–$C_4$ alkyl.

Particularly preferred compounds of Formula I are those where $R_1$ and $R_2$ are independently hydrogen or methyl, $R_4$ and $R_5$ are ethyl or propyl, preferably n-propyl, and $R_{10}$, $R_{11}$, X, Y and Z are independently hydrogen, methyl, or halogen. Preferably, the phenyl group carrying $R_{10}$, $R_{11}$, X, Y and Z is phenyl substituted in the 2- and 5-positions independently with methyl, ethyl, or halogen, preferably chloro or fluoro, or in the 3-position with methyl, ethyl or halogen. More preferably, the phenyl group is substituted in the 2- and 5-positions with halogen, preferably chloro or fluoro, or in the 3-position with hydrogen. Where phenyl is disubstituted with halogen, the halogens are preferably the same.

Other preferred compounds of the invention include those of Formulas II or III, wherein the variables are as defined above for Formula I:

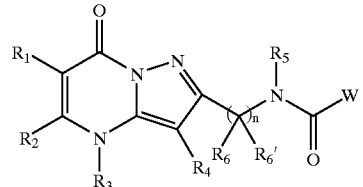

Formula II

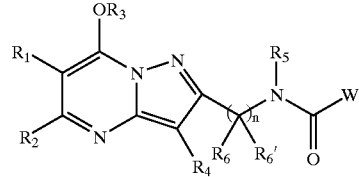

Formula III

More preferred compounds of Formulas II and III include those of Formulas IV, V, and VI:

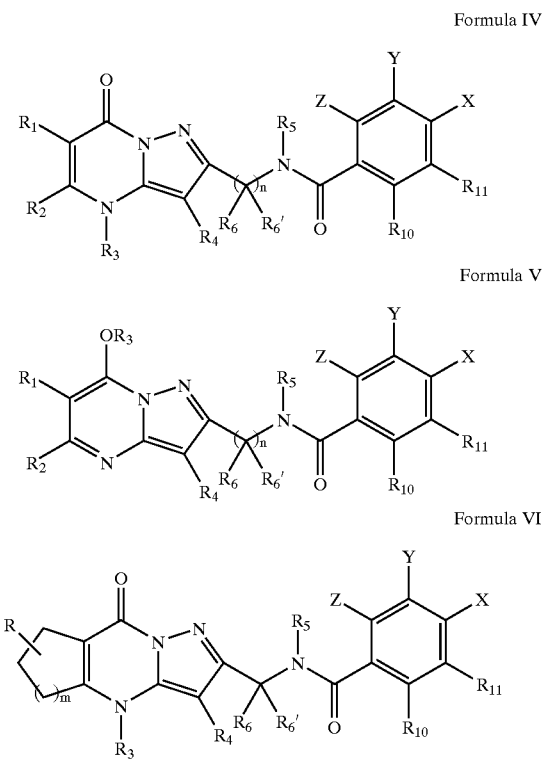

Formula IV

Formula V

Formula VI or a pharmaceutically acceptable salt thereof, wherein:
n, $R_1$, $R_2$, $R_3$, $R_4$, $R_5$, $R_6$ and $R_6'$ are as described above; m is 1, 2 or 3;

$R_{10}$, $R_{11}$, X, Y and Z are independently selected from hydrogen, halogen, hydroxy, amino, mono- and di($C_1$–$C_6$) alkyl amino, halo($C_1$–$C_6$)alkyl, halo($C_1$–$C_6$)alkoxy, $C_1$–$C_6$ alkyl, and $C_1$–$C_6$ alkoxy; and R represents up to 5 groups independently chosen from hydrogen, halogen, hydroxy, amino, halo($C_1$–$C_6$)alkyl, halo($C_1$–$C_6$)alkoxy, $C_1$–$C_6$ alkyl, and $C_1$–$C_6$ alkoxy.

Within Formulas IV–VI, n and m are each independently 1, 2 or 3; preferably n is 1. $R_1$ and $R_2$ are (i) are independently chosen from hydrogen, halogen, hydroxy, amino, halo($C_1$–$C_6$)alkyl, halo($C_1$–$C_6$)alkoxy, $C_1$–$C_6$ alkyl (preferably $C_1$–$C_3$ alkyl, more preferably methyl), and $C_1$–$C_6$ alkoxy or (ii) together with the carbon atoms with which they are attached, form a partially saturated or unsaturated carbocyclic ring of from 3 to 8 carbon atoms, wherein the ring is optionally substituted by up to three substituents independently chosen from halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy. Preferred $R_1$ and $R_2$ groups include hydrogen, methyl, and groups that together form a 5- or 6-membered optionally substituted ring.

For Formulas IV, V, and VI, $R_3$, $R_4$ and $R_5$ are independently chosen from (i) hydrogen; and (ii) $C_1$–$C_6$ acyl and $C_1$–$C_6$ alkyl, optionally substituted with up to three substituents independently chosen from halogen, hydroxy, halo ($C_1$–$C_2$)alkyl, halo($C_1$–$C_2$)alkoxy, methoxy, ethoxy, $C_3$–$C_7$ cycloalkyl, phenyl, pyridyl, and pyrimidyl, wherein each of phenyl, pyridyl, and pyrimidyl is optionally substituted with up to three groups selected independently from halogen, $C_1$–$C_6$ alkyl, $C_1$–$C_6$ alkoxy, hydroxy and amino. Preferred $R_3$ groups are hydrogen, methyl and ethyl; preferred $R_4$ and $R_5$ groups are $C_2$–$C_6$ alkyl and benzyl.

For Formulas IV, V, and VI, $R_6$ and $R_6'$ are independently selected at each occurrence from hydrogen and $C_1$–$C_6$ alkyl, with hydrogen being preferred for certain embodiments.

For Formulas IV, V, and VI, $R_{10}$, $R_{11}$, X, Y and Z are independently selected from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy, with hydrogen, halogen, methyl and methoxy being preferred.

R, in Formula VI, preferably represents (i) up to four, more preferably three, ring substituents when is 2, (ii) up to three, more preferably 2, ring substitutuents when is 1, and (iii) up to five substitutuents when is 3, where the substituents are independently chosen from hydrogen, halogen, hydroxy, amino, halo($C_1$–$C_6$)alkyl, halo($C_1$–$C_6$)alkoxy, $C_1$–$C_6$ alkyl and $C_1$–$C_6$ alkoxy.

Preferred compounds of Formula IV include those in which $R_1$, $R_2$ and $R_3$ are independently chosen from hydrogen, methyl, and ethyl; $R_4$ and $R_5$ are independently chosen from $C_2$–$C_6$ alkyl and benzyl; $R_6$ and $R_6'$ are both hydrogen; and $R_{10}$, $R_{11}$, X, Y and Z are independently selected from hydrogen, halogen and methyl. More preferred compounds of Formula IV are those where $R_1$ and $R_2$ are independently hydrogen or methyl, $R_3$ is methyl, $R_4$ and $R_5$ are ethyl or propyl, preferably n-propyl, and $R_{10}$, $R_{11}$, X, Y and Z are independently hydrogen, methyl, or halogen. Preferably, the phenyl group carrying $R_{10}$, $R_{11}$, X, Y and Z is phenyl substituted in the 2- and 5-positions independently with methyl, ethyl, or halogen, preferably chloro or fluoro, or in the 3-position with methyl, ethyl or halogen. More preferably, the phenyl group is substituted in the 2- and 5-positions with halogen, preferably chloro or fluoro, or in the 3-position with hydrogen. Where phenyl is disubstituted with halogen, the halogens are preferably the same.

Preferred compounds of Formula V include those in which $R_1$ and $R_2$ are independently chosen from hydrogen, methyl and ethyl; $R_3$ is methyl or ethyl; $R_6$ and $R_6'$ are both hydrogen; and S, T, X, W, Y and Z are independently chosen from hydrogen, halogen, methyl and methoxy.

Preferred compounds of Formula VT include those in which m is 1, and R, $R_6$, and $R_6'$ are hydrogen. Other preferred compounds of Formula VI include compounds where m is 1; R, $R_6$, and $R_6'$ are hydrogen; $R_3$ is chosen from hydrogen, methyl and ethyl; $R_4$ and $R_5$ are independently chosen from $C_2$–$C_6$ alkyl; and $R_{10}$, $R_{11}$, X, W, Y and Z are independently chosen from hydrogen, halogen and methyl. Still other preferred compounds of Formula VI include those in which $R_1$, $R_2$ and $R_3$ are independently chosen from hydrogen, methyl, and ethyl; $R_4$ and $R_5$ are independently chosen from $C_2$–$C_6$ alkyl and benzyl; $R_6$ and $R_6'$ are both hydrogen; and $R_{10}$, $R_{11}$, X, Y and Z are independently selected from hydrogen, halogen and methyl. More preferred compounds of Formula VI are those where $R_1$ and $R_2$ are independently hydrogen or methyl, $R_3$ is methyl, $R_4$ and $R_5$ are ethyl or propyl, preferably n-propyl, and $R_{10}$, $R_{11}$, X, Y and Z are independently hydrogen, methyl, or halogen. Preferably, the phenyl group carrying $R_{10}$, $R_{11}$, X, Y and Z is phenyl substituted in the 2- and 5-positions independently with methyl, ethyl, or halogen, preferably chloro or fluoro, or in the 3-position with methyl, ethyl or halogen. More preferably, the phenyl group is substituted in the 2- and 5-positions with halogen, preferably chloro or fluoro, or in the 3-position with hydrogen. Where phenyl is disubstituted with halogen, the halogens are preferably the same.

The following numbering system is used to identify positions on the pyrazolopyrimidine ring system of the compounds of the invention:

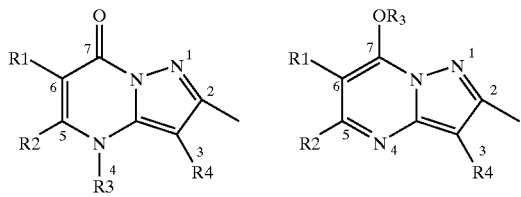

Representative compounds of the present invention include, but are not limited to, the compounds set forth in Tables A and I–III below, as well as the pharmaceutically acceptable acid and base addition salts thereof.

TABLE A

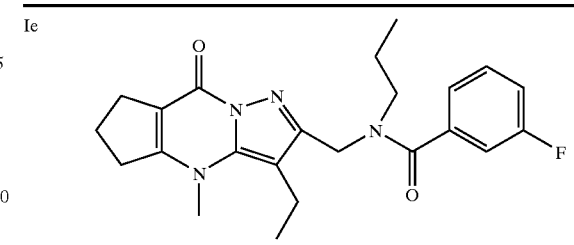

The following representative compounds are listed to provide the reader an understanding of the compounds encompassed by the invention.

N-[(5-methyl-7-oxo-3-propyl(4,7-dihydropyrazolo[1,5a]pyrimidin-2-yl))methyl]-N-propyl(3-fluorophenyl)carboxamide;

N-[(4,5-dimethyl-7-oxo-3-propyl(4,7-dihydropyrazolo[1,5a]pyrimidin-2-yl))methyl]-N-propyl(3-fluorophenyl)carboxamide;

N-[(5-methyl-7-oxo-3-propyl(4,7-dihydropyrazolo[1,5a]pyrimidin-2-yl))methyl]-N-(2-methylpropyl)(3-fluorophenyl)carboxamide;

N-[(4,5-dimethyl-7-oxo-3-propyl(4,7-dihydropyrazolo[1,5a]pyrimidin-2-yl))methyl]-N-(2-methylpropyl)(3-fluorophenyl)carboxamide;

N-[(3-ethyl-4,5-dimethyl-7-oxo(4,7-dihydropyrazolo[1,5a]pyrimidin-2-yl))methyl]-N-(2-methylpropyl)(3-fluorophenyl)carboxamide;

N-[(4-ethyl-5-methyl-7-oxo-3-propyl(4,7-dihydropyrazolo[1,5a]pyrimidin-2-yl))methyl]-N-propyl(3-fluorophenyl)carboxamide;

N-[(3-ethyl-5,6-dimethyl-7-oxo(4,7-dihydropyrazolo[1,5a]pyrimidin-2-yl))methyl]-N-propyl(3-fluorophenyl)carboxamide;

N-[(3-ethyl-4,5,6-trimethyl-7-oxo(4,7-dihydropyrazolo[1,5a]pyrimidin-2-yl))methyl]-N-propyl(3-fluorophenyl)carboxamide; N-[(4,5-dimethyl-7-oxo-3-propyl(4,7-dihydropyrazolo[1,5a]pyrimidin-2-yl))methyl]-N-(methylpropyl)(3-fluorophenyl)carboxamide;

N-[(4,5-dimethyl-7-oxo-3-propyl(4,7a-dihydropyrazolo[1,5a]pyrimidin-2-yl))methyl]-N-(ethylpropyl)(3-fluorophenyl)carboxamide;

N-[(4,5-dimethyl-7-oxo-3-propyl(4,7a-dihydropyrazolo[1,5a]pyrimidin-2-yl))methyl]-N-benzyl(3-fluorophenyl)carboxamide;

N-[(5,6-dimethyl-7-oxo-3-propyl(4,7a-dihydropyrazolo[1,5a]pyrimidin-2-yl))methyl]-N-propyl(3-fluorophenyl)carboxamide;

N-propyl-N-[(4,5,6-trimethyl-7-oxo-3-propyl(4,7-dihydropyrazolo [1,5a]pyrimidin-2-yl))methyl](3-fluorophenyl)carboxamide;

N-[(3-ethyl-5-methyl-7-oxo(4,7-dihydropyrazolo[1,5a]pyrimidin-2-yl))methyl]-N-(2-methylpropyl)(3-chlorophenyl)carboxamide;

N-[(3-ethyl-4,5-dimethyl-7-oxo(4,7-dihydropyrazolo[1,5a]pyrimidin-2-yl))methyl]-N-(2-methylpropyl)(3-chlorophenyl)carboxamide;

N-[(4,5-dimethyl-7-oxo-3-propyl(4,7-dihydropyrazolo[1,5a]pyrimidin-2-yl))methyl]-N-(methylpropyl)(3-chlorophenyl)carboxamide;

N-[(4,5-dimethyl-7-oxo-3-propyl(4,7-dihydropyrazolo[1,5a]pyrimidin-2-yl))methyl]-N-(ethylpropyl)(3-chlorophenyl)carboxamide;

N-[(4,5-dimethyl-7-oxo-3-propyl(4,7-dihydropyrazolo[1,5a]pyrimidin-2-yl))methyl]-N-benzyl(3-chlorophenyl) carboxamide;

N-[(5,6-dimethyl-7-oxo-3-propyl(4,7-dihydropyrazolo[1,5a]pyrimidin-2-yl))methyl]-N-propyl(3-chlorophenyl)carboxamide;

N-propyl-N-[(4,5,6-trimethyl-7-oxo-3-propyl (4,7-dihydropyrazolo [1,5a]pyrimidin-2-yl))methyl](3-chlorophenyl)carboxamide;

N-[(5-methyl-7-oxo-3-propyl(4,7-dihydropyrazolo[1,5a]pyrimidin-2-yl))methyl]-N-(2-methylpropyl)(2,5-difluorophenyl)carboxamide;

N-[(4,5-dimethyl-7-oxo-3-propyl(4,7-dihydropyrazolo[1,5a]pyrimidin-2-yl))methyl]-N-(2-methylpropyl)(2,5-difluorophenyl) carboxamide;

N-ethyl-N-[(3-ethyl-5-methyl-7-oxo(4,7-dihydropyrazolo[1,5a]pyrimidin-2-yl))methyl](2,5-difluorophenyl)carboxamide;

N-[(3-ethyl-4,5-dimethyl-7-oxo(4,7-dihydropyrazolo[1,5a]pyrimidin-2-yl))methyl]-N-(2-methylpropyl)(2,5-difluorophenyl)carboxamide;

N-[(4,5-dimethyl-7-oxo-3-propyl (4,7-dihydropyrazolo[1,5a]pyrimidin-2-yl))methyl]-N-(methylpropyl)(2,5-difluorophenyl)carboxamide;

N-[(4,5-dimethyl-7-oxo-3-propyl(4,7-dihydropyrazolo[1,5a]pyrimidin-2-yl))methyl]-N-(ethylpropyl)(2,5-difluorophenyl)carboxamide;

N-[(4,5-dimethyl-7-oxo-3-propyl(4,7-dihydropyrazolo[1,5a]pyrimidin-2-yl))methyl]-N-benzyl(2,5-difluorophenyl)carboxamide;

N-[(5,6-dimethyl-7-oxo-3-propyl(4,7-dihydropyrazolo[1,5a]pyrimidin-2-yl))methyl]-N-propyl(2,5-difluorophenyl)carboxamide;

N-propyl-N-[(4,5,6-trimethyl-7-oxo-3-propyl(4,7-dihydropyrazolo [1,5a]pyrimidin-2-yl))methyl](2,5-difluorophenyl)carboxamide;

N-[(7-methoxy-5-methyl-3-propyl(pyrazolo[1,5-a]pyrimidin-2-yl))methyl]-N-(2-methylpropyl)(3-fluorophenyl)carboxamide;

N-[(7-methoxy-5-methyl-3-propyl(pyrazolo[1,5-a]pyrimidin-2-yl))methyl]-N-propyl(3-fluorophenyl)carboxamide;

N-[(3-ethyl-7-methoxy-5-methyl(pyrazolo[1,5-a]pyrimidin-2-yl))methyl]-N-(2-methylpropyl)(3-fluorophenyl)carboxamide;

N-[(3-ethyl-7-methoxy-5-methyl(pyrazolo[1,5-a]pyrimidin-2-yl))methyl]-N-(2-methylpropyl)(3-chlorophenyl)carboxamide;

N-[(7-methoxy-5-methyl-3-propyl(pyrazolo[1,5-a]pyrimidin-2-yl))methyl]-N-(2-methylpropyl)(2,5-difluorophenyl)carboxamide;

N-[(3-ethyl-7-methoxy-5-methyl(pyrazolo[1,5-a]pyrimidin-2-yl))methyl]-N-(2-methylpropyl)(2,5-difluorophenyl)carboxamide;

N-[(8-oxo-3-propyl(4,5,6,7,8a-pentahydrocyclopenta[2,1-d]pyrazolo[1,5a]pyrimidin-2-yl))methyl]-N-propyl(3-fluorophenyl)carboxamide;

N-[(4-methyl-8-oxo-3-propyl(4,5,6,7,8a-pentahydrocyclopenta[2,1-d]pyrazolo[1,5a]pyrimidin-2-yl))methyl]-N-propyl(3-fluorophenyl)carboxamide;

N-[(3-ethyl-8-oxo(4,5,6,7,8a-pentahydrocyclopenta[2,1-d]pyrazolo[1,5a]pyrimidin-2-yl))methyl]-N-propyl(3-fluorophenyl)carboxamide;

N-[(3-ethyl-4-methyl-8-oxo(4,5,6,7,8a-pentahydrocyclopenta[2,1-d]pyrazolo[1,5a]pyrimidin-2-yl))methyl]-N-propyl(3-fluorophenyl)carboxamide;

N-[(3-ethyl-8-oxo(4,5,6,7,8a-pentahydrocyclopenta[2,1-d]pyrazolo[1,5a]pyrimidin-2-yl))methyl]-N-propyl(3-chlorophenyl)carboxamide;

N-[(3-ethyl-4-methyl-8-oxo (4,5,6,7,8a-pentahydrocyclopenta[2,1-d]pyrazolo[1,5a]pyrimidin-2-yl))methyl]-N-propyl(3-chlorophenyl)carboxamide;

N-[(3-ethyl-8-oxo(4,5,6,7,8a-pentahydrocyclopenta[2,1-d]pyrazolo [1,5a]pyrimidin-2-yl))methyl]-N-propyl(2,5-difluorophenyl)carboxamide;

N-[(3-ethyl-4-methyl-8-oxo(4,5,6,7,8a-pentahydrocyclopenta[2,1-d]pyrazolo[1,5a]pyrimidin-2-yl))methyl]-N-propyl(2,5-difluorophenyl)carboxamide; and pharmaceutically acceptable salts thereof.

It will be apparent that the specific compounds recited above are illustrative examples of compounds provided herein, and are not intended to limit the scope of the present invention. As noted above, all compounds of the present invention may be present as a free base or as a physiologically acceptable acid addition salt. In addition, both chiral compounds and racemic mixtures are encompassed by the present invention.

The present invention further provides pharmaceutical compositions, comprising a compound as described above in combination with a physiologically acceptable carrier or excipient. The pharmaceutical composition is formulated as an injectable fluid, an aerosol, a cream, a gel, a pill, a tablet, a capsule, a syrup, or a transdermal patch. Packaged pharmaceutical compositions are also provided, comprising such a pharmaceutical composition in a container and instructions for using the composition to treat a patient suffering from anxiety, depression, a sleep disorder, attention deficit disorder, or Alzheimer's dementia.

Methods are provided for the treatment of anxiety, depression, a sleep disorder, attention deficit disorder, or Alzheimer's dementia, comprising administering to a patient in need of such treatment a therapeutically effective amount of a compound as described above. The patient may be a human or other mammal. Treatment of humans, domesticated companion animals (pets) or livestock animals suffering from certain CNS disorders with an effective amount of a compound of the invention is encompassed by the present invention.

The present invention also provides methods for potentiating a therapeutic effect of a CNS agent, comprising administering to a patient a CNS agent and a compound as described above.

Methods for determining the presence or absence of $GABA_A$ receptor in a sample are further provided, comprising: (a) contacting a sample with a compound as described above under conditions that permit binding of the compound to $GABA_A$ receptor; and (b) detecting a level of compound bound to $GABA_A$ receptor. Furthermore, the compounds as described above can be radiolabeled, wherein the step of detection comprises: (i) separating unbound compound from bound compound; and (ii) detecting the presence or absence of bound compound in the sample. When radiolabelled compounds are used, the presence or absence of bound compound is detected using autoradiography.

The present invention further provides a method for altering the signal-transducing activity of $GABA_A$ receptor, comprising contacting a cell expressing $GABA_A$ receptor with a compound as described above in an amount sufficient to detectably alter the electrophysiology of the cell.

More preferably, the cell recombinantly expresses a heterologous $GABA_A$ receptor, wherein the alteration of the electrophysiology of the cell is detected by intracellular recording or patch clamp recording.

More preferably, the cell is a neuronal cell that is contacted in vivo in an animal, the solution is a body fluid, and the alteration in the electrophysiology of the cell is detected as a change in the animal's behavior. Even more preferably the animal is a human, the cell is a brain cell, and the fluid is cerebrospinal fluid.

As noted above, the invention provides (oxo-pyrazolo[1,5a]pyrimidin-2-yl)alkyl-carboxamides, that preferably bind with high affinity and/or high selectivity to the benzodiazepine site of $GABA_A$ receptors, including human $GABA_A$ receptors. Preferably, in an assay of $GABA_A$ receptor binding, the above compounds exhibit an $K_i$ of 1 micromolar or less. More preferably, in an assay of $GABA_A$ receptor binding, the compound exhibits an $K_i$ of 100 nanomolar or less. Even more preferably, in an assay of $GABA_A$ receptor binding, the compound exhibits an $K_i$ of 10 nanomolar or less.

The above compounds are also useful for the manufacture of a medicament for the treatment of anxiety, depression, a sleep disorder, an attention deficit disorder, or Alzheimer's dementia.

Without wishing to be bound to any particular theory, it is believed that the interaction of the compounds provided herein with the benzodiazepine site results in the pharmaceutical utility of these compounds. Compounds provided herein may be used in a variety of in vivo and in vitro contexts, as discussed in further detail below.

The compounds provided herein detectably alter (modulate) ligand binding to $GABA_A$ receptor, as determined using a standard in vitro receptor binding assay. References herein to a "$GABA_A$ receptor ligand binding assay" are intended to refer to the standard in vitro receptor binding assay provided in Example 5. Briefly, a competition assay may be performed in which a $GABA_A$ receptor preparation is incubated with labeled (e.g., $^3H$) ligand, such as Flumazenil, and unlabeled test compound. Incubation with a compound that detectably modulates ligand binding to $GABA_A$ receptor will result in a decrease or increase in the amount of label bound to the $GABA_A$ receptor preparation, relative to the amount of label bound in the absence of the compound. Preferably, such a compound will exhibit a $K_i$ at a $GABA_A$ receptor of less than 1 micromolar, more preferably less than 500 nM, 100 nM, 20 nM or 10 nM. The $GABA_A$ receptor used to determine in vitro binding may be obtained from a variety of sources, for example from preparations of rat cortex or from cells expressing cloned human $GABA_A$ receptors.

If desired, compounds provided herein may be evaluated for certain pharmacological properties including, but not limited to, solubility, oral bioavailability, toxicity, serum protein binding, lack of clinically relevant EKG effect and in vitro and in vivo half-life. Routine assays that are well known in the art may be used to assess these properties, and identify superior compounds for a particular use. For example, solubility in aqueous solutions is preferably at least 500 ng/mL. Assays used to predict bioavailability include transport across human intestinal cell monolayers, including Caco-2 cell monolayers. Toxicity may be assessed using any standard method, such as the assay detecting an effect on cellular ATP production provided in Example 7, or toxicity to cultured hepatocytes. Penetration of the blood brain barrier of a compound in humans may be predicted from the brain levels of the compound in laboratory animals given the compound intravenously. Serum protein binding may be predicted from albumin binding assays. Such assays are described in a review by Oravcová, et al. (Journal of Chromatography B (1996) volume 677, pages 1–27). Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

For detection purposes, as discussed in more detail below, compounds provided herein may be isotopically-labeled or radiolabeled. Such compounds are identical to those described above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Compounds

Compounds provided herein may generally be prepared using standard synthetic methods. Starting materials are generally readily available from commercial sources, such as Sigma-Aldrich Corp. (St. Louis, Mo.). A representative route suitable for preparing compounds of the invention is shown in Scheme I. In addition, other synthetic routes similar to that shown in Scheme I may be used. Within Scheme I, the substituents $R_1$, $R_2$, $R_3$, $R_4$, $R_5$, $R_{10}$, $R_{11}$, X, Y and Z carry the definitions set forth above.

Scheme I:

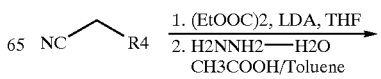

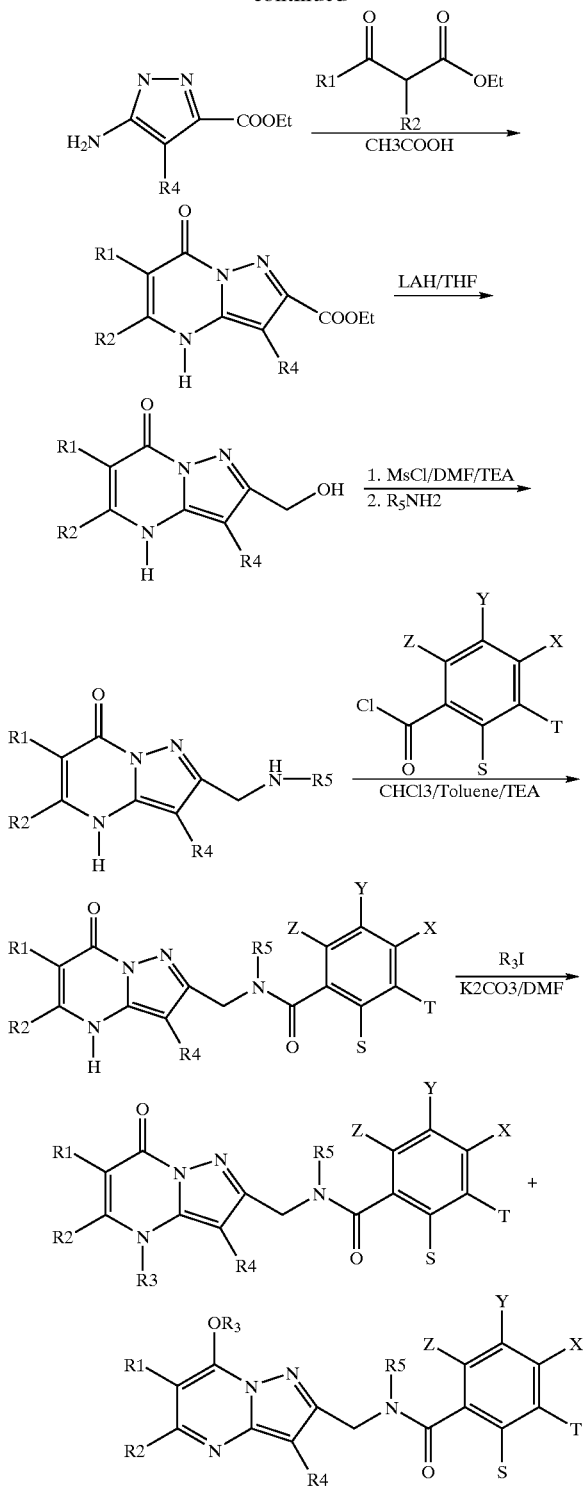

It will be apparent that the starting materials may be varied and additional steps employed to produce the varied compounds encompassed by the present invention. In some cases, protection of reactive functionalities may be necessary to achieve some of the above transformations. In general, such need for protecting groups, as well as the conditions necessary to attach and remove such groups, will be apparent to those skilled in the art of organic synthesis.

In certain situations, compounds provided herein may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Compounds may be radiolabeled by carrying out their synthesis using precursors comprising at least one atom that is a radioisotope. Such radioisotope(s) are preferably selected from carbon (preferably $^{14}C$), hydrogen (preferably $^{3}H$), sulfur (preferably $^{35}S$), or iodine (preferably $^{125}I$). Synthesis of such radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed above using the compound as substrate. In addition, certain precursors may be subjected to tritium-halogen exchange with tritium gas, tritium gas reduction of unsaturated bonds, or reduction using sodium borotritide, as appropriate. $^{14}C$ radiolabeled compounds of the invention may be prepared using $^{14}C$ radiolabeled diethyl oxalate (AMERICAN RADIOLABELED CHEMICALS, St. Louis, Mo., catalog no. ARC-1127) as a starting material for the synthesis outlined in Scheme I.

Pharmaceutical Compositions

The present invention also provides pharmaceutical compositions comprising at least one compound provided herein, together with at least one physiologically acceptable carrier or excipient. Such compounds may be used for treating disorders responsive to $GABA_A$ receptor modulation (e.g., treatment of anxiety, depression, sleep disorders or cognitive impairment by $GABA_A$ receptor modulation). Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs). If desired, other active ingredients may also be included, such as CNS agents.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with one or more excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectible aqueous or oleaginous suspension. The compound, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of active compound release. The amount of compound contained within a sustained release formulation depends upon the site of implantation, the rate and expected duration of release and the nature of the condition to be treated or prevented.

Compounds provided herein are generally present within a pharmaceutical composition in a therapeutically effective amount. A therapeutically effective amount is an amount that results in a discernible patient benefit, such as diminution of symptoms of a CNS disorder. A preferred concentration is one sufficient to inhibit the binding of $GABA_A$ receptor ligand to $GABA_A$ receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating a CNS disorder such as anxiety, depression, a sleep disorder, attention deficit disorder or Alzheimer's dementia. Packaged pharmaceutical compositions include a container holding a therapeutically effective amount of at least one compound as described herein and instructions (e.g., labeling) indicating that the contained composition is to be used for treating the CNS disorder.

Methods of Use

Within certain aspects, the present invention provides methods for inhibiting the development of a CNS disorder. In other words, therapeutic methods provided herein may be used to treat a disorder, or may be used to prevent or delay the onset of such a disease in a patient who is free of detectable CNS disorder. CNS disorders are discussed in more detail below, and may be diagnosed and monitored using criteria that have been established in the art. Patients may include humans, domesticated companion animals (pets, such as dogs) and livestock animals, with dosages and treatment regimes as described above.

Frequency of dosage may vary depending on the compound used and the particular disease to be treated or prevented. In general, for treatment of most disorders, a dosage regimen of 4 times daily or less is preferred. For the treatment of sleep disorders a single dose that rapidly reaches effective concentrations is desirable. Patients may generally be monitored for therapeutic effectiveness using assays suitable for the condition being treated or prevented, which will be familiar to those of ordinary skill in the art.

Within preferred embodiments, compounds provided herein are used to treat patients in need of such treatment, in an amount sufficient to alter the symptoms of a CNS disorder. Compounds that act as agonists at $\alpha_2\beta_3\gamma_2$ and $\alpha_3\beta_3\gamma_2$ receptor subtypes are particularly useful in treating anxiety disorders such as panic disorder, obsessive compulsive disorder and generalized anxiety disorder; stress disorders including post-traumatic stress, and acute stress disorders. Compounds that act as agonists at $\alpha_2\beta_3\gamma_2$ and $\alpha_3\beta_3\gamma_2$ receptor subtypes are also useful in treating depressive or bipolar disorders and in treating sleep disorders. Compounds that act as inverse agonists at the $\alpha_5\beta_3\gamma_2$ receptor subtype or $\alpha_1\beta_2\gamma_2$ and $\alpha_5\beta_3\gamma_2$ receptor subtypes are particularly useful in treating cognitive disorders including those resulting from Down Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

CNS disorders that can be treated using compounds and compositions provided herein include:

Depression, e.g., depression, atypical depression, bipolar disorder, depressed phase of bipolar disorder.

Anxiety, e.g., general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g., sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g., cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g., attention deficit disorder (ADD), and attention deficit and hyperactivity disorder (ADHD).

In a separate aspect, the present invention provides methods for potentiating the action (or therapeutic effect) of other CNS agent(s). Such methods comprise administering an effective amount of a compound provided herein in combination with another CNS agent. Such CNS agents include, but are not limited to the following: for anxiety, serotonin receptor (e.g., 5-HT$_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Within preferred embodiments, the present invention provides a method of potentiating the antidepressant activity of selective serotonin reuptake inhibitors (SSRIs) by administering an effective amount of a GABA agonist compound of the invention in combination with an SSRI. An effective amount of compound is an amount sufficient to result in a detectable change in patient symptoms, when compared to a patient treated with the other CNS agent alone.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339-45; or Le, et al., *Alcohol and Alcoholism* (1996) 31 Suppl. 127–132. See also the discussion of the use of the GABA$_A$ receptor ligand 3-(5-methylisoxazol-3-yl)-6-(1-methyl-1,2,3-triazol-4-yl)methyloxy-1,2,4-triazolo[3,4-a]phthalazine in combination with nicotinic agonists, muscarinic agonists and In addition, WO 99/37303 describes the use of a class of GABA$_A$ receptor ligands, 1,2,4-triazolo[4,3-b]pyridazines, in combination with SSRIs.

The present invention also pertains to methods of inhibiting the binding of benzodiazepine compounds, such as Ro15-1788, or GABA to the GABA$_A$ receptors. Such methods involve contacting a compound provided herein with cells expressing GABA$_A$ receptor, wherein the compound is present in an amount sufficient to inhibit benzodiazepine binding or GABA binding to GABA$_A$ receptors in vitro. This method includes inhibiting the binding of benzodiazepine compounds to GABA$_A$ receptors in vivo (e.g., in a patient given an amount of a compound provided herein that would be sufficient to inhibit the binding of benzodiazepine compounds or GABA to GABA$_A$ receptors in vitro). In one embodiment, such methods are useful in treating benzodiazepine drug overdose. The amount of a compound that would be sufficient to inhibit the binding of a benzodiazepine compound to the GABA$_A$ receptor may be readily determined via an GABA$_A$ receptor binding assay, such as the assay described in Example 5.

Within separate aspects, the present invention provides a variety of in vitro uses for the compounds provided herein. For example, such compounds may be used as probes for the detection and localization of GABA$_A$ receptors, in samples such as tissue sections, as positive controls in assays for receptor activity, as standards and reagents for determining the ability of a candidate agent to bind to GABA$_A$ receptor, or as radiotracers for positron emission tomography (PET) imaging or for single photon emission computerized tomography (SPECT). Such assays can be used to characterize GABA$_A$ receptors in living subjects. Such compounds are also useful as standards and reagents in determining the ability of a potential pharmaceutical to bind to GABA$_A$ receptor.

Within methods for determining the presence or absence of GABA$_A$ receptor in a sample, a sample may be incubated with a compound as provided herein under conditions that permit binding of the compound to GABA$_A$ receptor. The amount of compound bound to GABA$_A$ receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of capsaicin receptor in the sample. Detection assays, including receptor autoradiography (receptor mapping) of GABA$_A$ receptors in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well known cell culture and cell separation methods. For example, compounds may be linked to the interior surface of a tissue culture plate or other cell culture support, for use in immobilizing GABA$_A$ receptor-expressing cells for screens, assays and growth in culture. Such linkage may be performed by any suitable technique, such as the methods described above, as well as other standard techniques. Compounds may also be used to facilitate cell identification and sorting in vitro, permitting the selection of cells expressing a GABA$_A$ receptor. Preferably, the compound(s) for use in such methods are labeled as described herein. Within one preferred embodiment, a compound linked to a fluorescent marker, such as fluorescein, is contacted with the cells, which are then analyzed by fluorescence activated cell sorting (FACS).

Within other aspects, methods are provided for modulating binding of ligand to a GABA$_A$ receptor in vitro or in vivo, comprising contacting a GABA$_A$ receptor with a sufficient amount of a compound provided herein, under conditions suitable for binding of ligand to the receptor. The GABA$_A$ receptor may be present in solution, in a cultured or isolated cell preparation or within a patient. Preferably, the GABA$_A$ receptor is a present in the brain of a mammal. In general, the amount of compound contacted with the receptor should be sufficient to modulate ligand binding to GABA$_A$ receptor in vitro within, for example, a binding assay as described in Example 5.

Also provided herein are methods for altering the signal-transducing activity of cellular GABA$_A$ receptor (particularly the chloride ion conductance), by contacting GABA$_A$ receptor, either in vitro or in vivo, with a sufficient amount of a compound as described above, under conditions suitable for binding of ligand to the receptor. The GABA$_A$ receptor may be present in solution, in a cultured or isolated cell preparation or within a patient. In general, the amount of compound contacted with the receptor should be sufficient to modulate ligand binding to GABA$_A$ receptor in vitro within, for example, a binding assay as described in Example 5. An effect on signal-transducing activity may be assessed as an alteration in the electrophysiology of the cells, using standard techniques. Tf the receptor is present in an animal, an alteration in the electrophysiology of the cell may be detected as a change in the animal's feeding behavior. The amount of a compound that would be sufficient to alter the signal-transducing activity of GABA$_A$ receptors may be determined via a GABA$_A$ receptor signal transduction assay, such as the assay described in Example 6. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of GABA$_A$ receptors in vitro may be determined from a detectable change in the electrophysiology of cells expressing GABA$_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing GABA$_A$ receptors has occurred.

The following Examples are offered by way of illustration and not by way of limitation. Unless otherwise specified all reagents and solvent are of standard commercial grade and are used without further purification.

EXAMPLES

Example 1

Preparation of Starting Materials and Intermediates

The starting materials and various intermediates may be obtained from commercial sources, prepared from commercially available organic compounds, or prepared using well known synthetic methods. Representative examples of methods for preparing intermediates of the invention are set forth below.

A. Preparation of ethyl 5-amino-4-propylpyrazolo-3-carboxylate

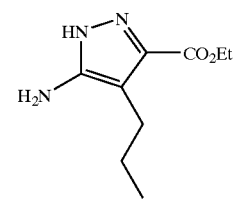

144 mL of 2M lithium diisopropylamide in heptane/tetrahydrofuran/ethylbenzene at −78° C. is added to a solution of 20 g valeronitrile in 50 mL of tetrahydrofuran. The mixture is stirred at −78° C. for 1 hour, and then added to a solution of 35.2 g of diethyloxalate in 100 mL of tetrahydrofuran. The resulting solution is stirred at −78° C. for 3 hours. The reaction is quenched by addition of aqueous NH₄Cl solution followed by 3N HCl. The reaction mixture is transferred to a separatory funnel and extracted with ethyl acetate. The organic layer is washed with brine, dried over sodium sulfate, filtered, and evaporated to give a brown oil. The oil, 23.3 g of hydrazine monohydrate, 43 mL of acetic acid and 430 mL of toluene are refluxed overnight using a Dean Stark trap. The solvent is removed in vacuo, and the residue partitioned between ethyl acetate and saturated sodium bicarbonate. The organic layer is dried over sodium sulfate and filtered. The solvent is removed in vacuo, and the residue is purified by silica gel column chromatography eluting with ethyl acetate:hexanes=1:1 to give 12.1 g of the title compound as an off-white solid. $^1$H NMR (CDCl₃) δ: 0.95 (t, 3H), 1.38 (t, 3H), 1.55 (m, 2H), 2.58 (t, 2H), 4.36 (q, 2H). LC-MS (APCI, m/z) 198 (M+1).

B. Preparation of ethyl 5-methyl-3-propyl-7-oxo-4,7-dihydropyrazolo[1,5-a]pyrimidine-2-carboxylate

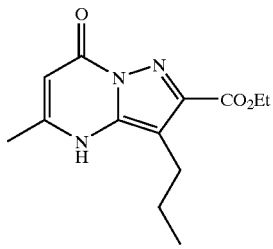

A mixture of 11.5 g of ethyl 5-amino-4-propylpyrazole-3-carboxylate, 11.3 g of ethyl acetoacetate, and 100 mL of acetic acid is refluxed overnight. The solvent is removed in vacuo, and the residue triturated with hexane/ether (1:1) to give 14.8 g of off-white solid. $^1$H NMR (CD₃OD) δ: 0.97 (t, 3H), 1.40 (t, 3H), 1.61 (m, 2H), 2.42 (s, 3H), 2.85 (t, 2H), 4.40 (q, 2H), 5.73 (s, 1H). LC-MS (APCI, m/z): 264 (M+1).

C. Preparation of 2-(hydroxymethyl)-5-methyl-3-propyl-4,7-dihydropyrazolo[1,5a]pyrimidin-7-one

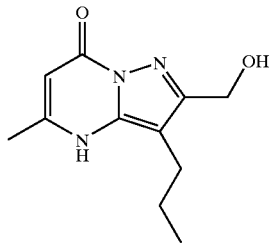

To a solution of 14.8 g of ethyl 5-methyl-7-oxo-3-propyl-4,7-dihydropyrazolo[1,5-a]pyrimidine-2-carboxylate in 600 mL of tetrahydrofuran, is added 67.5 mL of 1 M lithium aluminum hydride in tetrahydrofuran. The reaction mixture is stirred for 1 hour at 0° C. then quenched with sodium carbonate decahydrate and filtered through Celite. The filtrate is concentrated in vacuo to give 10.9 g of yellow solid.

$^1$H NMR (CD₃OD) δ: 0.96 (t, 3H), 1.62 (m, 2H), 2.38 (s, 3H), 2.65 (t, 2H), 4.65 (s, 2H), 5.62 (s, 1H). LC-MS (APCI, m/z): 222 (M+1).

D. Preparation of 5-methyl-3-propyl-2-[(propylamino)methyl]-4,7-dihydropyrazolo[1,5a]pyrimidin-7-one

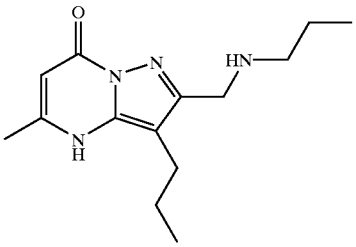

1.4 g of methanesulfonyl chloride is added to a solution of 1.6 g of 2-(hydroxymethyl)-5-methyl-3-propyl-4,7a-dihydropyrazolo[1,5a]pyrimidin-7-one in 70 mL of chloroform, 10 mL of N,N-dimethylformamide and 1.8 mL of triethylamine. The reaction mixture is stirred at 0° C. for 2 hours. The solution is then added to 20 mL propylamine and stirred at room temperature overnight. The solvent is removed in vacuo, and the residue purified by silica gel chromatography eluting with CHCl₃:MeOH:TEA=90:10:1 to give 0.91 g of the title compound as a yellow solid. $^1$H NMR (CD₃OD) δ: 0.80 (br s, 3H), 0.95 (t, 3H), 1.40 (br s, 2H), 1.68 (m, 2H), 2.33 (s, 3H), 2.54 (br s, 2H), 2.93 (t, 2H), 4.27 (s, 2H), 5.76 (s, 1H). LC-MS (APCI, m/z): 263 (M+1).

Example 2

Preparation of N-[(5-methyl-7-oxo-3-propyl(4,7-dihydropyrazolo[1,5a]pyrimidin-2-yl))methyl]-N-propyl(3-fluorophenyl)carboxamide

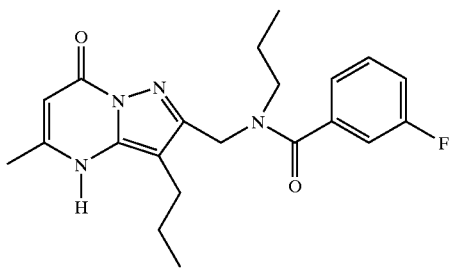

To a solution of 0.6 g of 5-methyl-3-propyl-2-[(propylamino)methyl]-4,7-dihydropyrazolo[1,5a]pyrimidin-7-one in 10 mL of CHCl₃ and 1 mL of TEA is added 0.55 g of 3-fluorobenzoyl chloride in 17 mL of toluene. The reaction mixture is stirred at room temperature for 3 hours. The reaction is quenched by the addition of water then transferred to a separatory funnel. The organic layer is washed with brine, dried over sodium sulfate, and filtered. The solvent is removed in vacuo and the residue purified by silica gel chromatography and eluted with EA:MeOH:TEA=10:2:1 to give 0.67 g of the title compound as a yellow solid. $^1$H NMR data listed in table 1. LC-MS (APCI, m/z): 385 (M+1).

Example 3

Preparation of N-[(4,5-dimethyl-7-oxo-3-propyl(4,7-dihydropyrazolo[1,5a]pyrimidin-2-yl))methyl]-N-propyl(3-fluorophenyl)carboxamide and N-[(7-methoxy-5-methyl-3-propyl(7a-hydropyrazolo[1,5a]pyrimidin-2yl))methyll-N-propyl(3-fluorophenyl) carboxamide

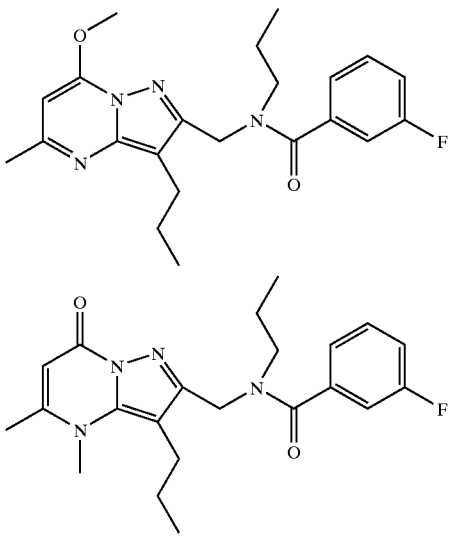

72.4 mg of iodomethane is added to a solution of 130 mg of N-[(5-methyl-7-oxo-3-propyl(4,7a-dihydropyrazolo[1,5a]pyrimidin-2-yl))methyl]-N-propyl(3-fluorophenyl) carboxamide and 70.4 mg of potassium carbonate in 5 mL of N,N-dimethylformamide. The reaction mixture is stirred at room temperature overnight. The reaction mixture is diluted with ethyl acetate, washed with water and brine, dried over sodium sulfate, and filtered. The solvent is removed in vacuo and the residue purified by preparative TLC, eluting with $CH_2Cl_2$:MeOH=9:1 to give 60 mg of N-[(4,5-dimethyl-7-oxo-3-propyl(4,7-dihydropyrazolo[1,5a]pyrimidin-2-yl))methyl]-N-propyl(3-fluorophenyl)carboxamide as a yellow oil and 50 mg of N-[(7-methoxy-5-methyl-3-propyl(7a-hydropyrazolo[1,5a]pyrimidin-2yl))methyl]-N-propyl(3-fluorophenyl) carboxamide as an off-white solid). $^1$H NMR data are listed in Tables I–III respectively. LC-MS (APCT, m/z): 399 (M+1).

Example 4

The following compounds (Table I, II and III) are prepared essentially according to the procedures described above. Most of the compounds exist as mixtures of rotamers, H and H' denote major and minor forms respectively.

TABLE 1

| No. | R1 | R2 | R3 | R4 | R5 | X | Name | $^1$H NMR (CDCl$_3$) δ | H/H' |
|---|---|---|---|---|---|---|---|---|---|
| 1 | H | CH$_3$ | H | Propyl | Propyl | 3-Fluoro | N-[(5-methyl-7-oxo-3-propyl (4,7-dihydropyrazolo [1,5a]pyrimidin-2-yl))methyl]-N-propyl (3-fluorophenyl)carboxamide | 0.60–0.90 (m, 6H + 6H'), 1.40–1.60 (m, 4H + 4H'), 2.20–2.63 (m, 5H + 5H'), 3.16 (t, 2H), 3.36 (br s, 2H'), 4.73 (s, 2H), 4.53 (s, 2H'), 5.51 (s, 1H), 5.53 (s, 1H'), 7.03–7.37 (m, 4H + 4H') | 4/1 |
| 2 | H | CH$_3$ | CH$_3$ | Propyl | Propyl | 3-Fluoro | N-[(4,5-dimethyl-7-oxo-3-propyl (4,7-dihydropyrazolo[1,5a]pyrimidin-2-yl))methyl]-N-propyl (3-fluorophenyl)carboxamide | 0.67 (t, 3H), 0.84 (br s, 3H'), 1.04 (t, 3H), 0.91 (br s, 3H'), 1.30–1.70 (m, 4H + 4H'), 2.39 (s, 3H), 2.36 (s, 3H'), 2.80 (t, 2H), 2.43 (br s, 2H'), 3.20 (t, 2H), 3.42 (br s, 2H'), 3.80 (s, 3H), 3.75 (s, 3H'), 4.95 (s, 2H), 4.64 (s, 2H'), 5.73 (s, 1H + 1H'), 7.04–7.44 (m, 4H + 4H') | 4/1 |
| 3 | H | CH$_3$ | H | Propyl | isobutyl | 3-Fluoro | N-[(5-methyl-7-oxo-3-propyl (4,7-dihydropyrazolo[1,5a]pyrimidin-2-yl))methyl]-N-(2-methylpropyl)(3-fluorophenyl)carboxamide | 0.60–0.87 (m, 9H + 9H'), 1.46 (br s, 2H + 2H'), 1.98 (m, 1H + 1H'), 2.08–2.60 (m, 5H + 5H'), 3.09 (d, 2H), 3.20 (d, 2H'), 4.81 (s, 2H), 4.56 (s, 2H'), 5.56 (s, 1H), 5.63 (s, 1H'), 7.01–7.39 (m, 4H + 4H') | 3/1 |
| 4 | H | CH$_3$ | CH$_3$ | Propyl | isobutyl | 3-Fluoro | N-[(4,5-dimethyl-7-oxo-3-propyl (4,7-dihydropyrazolo[1,5a]pyrimidin-2-yl))methyl]-N-(2-methylpropyl)(3- | 0.69 (d, 6H), 0.96 (d, 6H'), 0.85 (t, 3H), 1.02 (t, 3H'), 1.57 (m, 2H + 2H'), 2.16 (m, 1H + 1H'), 2.38 (s, 3H + 3H'), 2.80 (t, 2H + 2H'), 3.09 (d, 2H), 3.25 (d, 2H'), 3.80 | 3/1 |

TABLE 1-continued

| No. | R1 | R2 | R3 | R4 | R5 | X | Name | ¹H NMR (CDCl₃) δ | H/H' |
|---|---|---|---|---|---|---|---|---|---|
| | | | | | | | fluorophenyl)carboxamide | (s, 3H), 3.73 (s, 3H'), 4.92 (s, 2H), 4.65 (s, 2H'), 5.75 (s, 1H + 1H'), 7.04–7.41 (m, 4H + 4H') | |
| 5 | H | CH₃ | CH₃ | Ethyl | isobutyl | 3-Fluoro | N-[(3-ethyl-4,5-dimethyl-7-oxo (4,7-dihydropyrazolo[1,5a]pyrimidin-2-yl))methyl]-N-(2-methylpropyl)(3-fluorophenyl)carboxamide | 0.71 (d, 6H), 0.91 (d, 6H'), 1.25 (t, 3H), 1.04 (t, 3H'), 2.16 (m, 1H + 1H'), 2.35 (s, 3H + 3H'), 2.85 (q, 2H), 2.47 (q, 2H'), 3.08 (d, 2H), 3.23 (d, 2H'), 3.80 (s, 3H) 3.71 (s, 3H'), 4.93 (s, 2H), 4.64 (s, 2H'), 5.69 (s, 1H + 1H'), 7.04–7.43 (m, 4H + 4H') | 3/1 |
| 6 | H | CH₃ | Ethyl | Propyl | Propyl | 3-Fluoro | N-[(4-ethyl-5-methyl-7-oxo-3-propyl(4,7-dihydropyrazolo[1,5a]pyrimidin-2-yl))methyl]-N-propyl(3-fluorophenyl)carboxamide | 0.69 (m, 3H), 0.83 (m, 3H'), 1.05 (t, 3H), 0.94 (m, 3H'), 1.38 (t, 3H + 3H'), 1.47–1.70 (m, 4H + 4H'), 2.42 (s, 3H + 3H'), 2.69 (t, 2H), 2.31 (br s, 2H'), 3.22 (t, 2H), 3.44 (br s, 2H'), 4.15 (q, 2H), 4.04 (br s, 2H'), 4.96 (s, 2H), 4.65 (s, 2H'), 5.76 (s, 1H + 1H'), 7.05–7.41 (m, 4H + 4H') | 3/1 |
| 7 | CH₃ | CH₃ | H | Ethyl | Propyl | 3-Fluoro | N-[(3-ethyl-5,6-dimethyl-7-oxo (4,7-dihydropyrazolo[1,5a]pyrimidin-2-yl))methyl]-N-propyl(3-fluorophenyl)carboxamide | 0.50–1.08 (m, 6H + 6H'), 1.50 (m, 2H + 2H'), 2.07 (s, 3H + 3H'), 2.23–2.65 (m, 5H + 5H'), 3.10 (br s, 2H), 3.30 (br s, 2H'), 4.83 (s, 2H), 4.50 (s, 2H'), 7.00–7.62 (m, 4H + 4H') | 3/1 |
| 8 | CH₃ | CH₃ | CH₃ | Ethyl | Propyl | 3-Fluoro | N-[(3-ethyl-4,5,6-trimethyl-7-oxo(4,7-dihydropyrazolo[1,5a]pyrimidin-2-yl))methyl]-N-propyl(3-fluorophenyl)carboxamide | 0.68 (t, 3H), 0.90 (t, 3H'), 1.23 (t, 3H), 1.05 (br s, 3H'), 1.60 (m, 2H + 2H'), 2.18 (s, 3H + 3H'), 2.40 (s, 3H + 3H'), 2.88 (q, 2H), 2.49 (q, 2H'), 3.20 (t, 2H), 3.40 (br s, 2H'), 3.83 (s, 2H), 3.77 (s, 2H'), 4.95 (s, 2H), 4.64 (s, 2H'), 7.05–7.43 (m, 4H + 4H') | 4/1 |
| 9 | H | CH₃ | CH3— | Propyl | secbutyl | 3-Fluoro | N-[(4,5-dimethyl-7-oxo-3-propyl(4,7-dihydropyrazolo[1,5a]pyrimidin-2-yl))methyl]-N-(methylpropyl)(3-fluorophenyl)carboxamide | 0.76 (t, 3H), 1.02 (t, 3H), 1.16 (d, 3H), 1.40–1.89 (m, 4H), 2.35 (s, 3H), 2.87 (t, 2H), 3.67–3.80 (m, 4H), 4.55 (d, 1H), 5.10 (d, 1H), 5.70 (s, 1H), 7.05–7.40 (m, 4H) | |
| 10 | H | CH₃ | CH₃ | Propyl | (CH₃CH₂)₂CH— | 3-Fluoro | N-[(4,5-dimethyl-7-oxo-3-propyl(4,7-dihydropyrazolo[1,5a]pyrimidin-2-yl))methyl]-N-(ethylpropyl)(3-fluorophenyl) carboxamide | 0.75 (t, 6H), 0.87 (t, 6H'), 1.02 (t, 3H), 0.95 (t, 3H'), 1.40–1.60 (m, 6H + 6H'), 2.35 (s, 3H + 3H'), 2.88 (t, 2H), 2.43 (t, 2H'), 3.48 (m, 1H + 1H'), 3.77 (s, 3H), 3.70 (s, 3H'), 4.80 (s, 2H), 4.52 (s, 2H'), 5.69 (s, 1H + 1H'), 7.05–7.40 (m, 4H + 4H') | 5/1 |
| 11 | H | CH₃ | CH₃ | Propyl | benzyl | 3-Fluoro | N-[(4,5-dimethyl-7-oxo-3-propyl(4,7-dihydropyrazolo[1,5a]pyrimidin-2-yl))methyl]-N-benzyl(3-fluorophenyl)carboxamide | 1.00 (t, 3H), 0.73 (br s, 3H'), 1.58 (m, 2H), 1.23 (m, 2H'), 2.36 (s, 3H + 3H'), 2.80 (t, 2H), 2.25 (br s, 2H'), 3.76 (s, 3H), 3.63 (s, 3H'), 4.68 (s, 2H), 4.53 (s, 2H'), 4.84 (s, 2H + 2H'), 5.73 (s, 1H + 1H'), 7.04–7.40 (m, 9H + 9H') | 3/1 |
| 12 | CH₃ | CH₃ | H | Propyl | Propyl | 3-Fluoro | N-[(5,6-dimethyl-7-oxo-3-propyl(4,7-dihydropyrazolo[1,5a]pyrimidin-2-yl))methyl]-N-propyl(3-fluorophenyl)carboxamide | 0.63–0.97 (m, 6H + 6H'), 1.40–1.80 (m, 4H + 4H'), 2.05 (s, 3H + 3H'), 2.20–2.56 (m, 5H + 5H'), 3.24 (m, 2H + 2H'), 4.81 (s, 2H), 4.57 (s, 2H'), 7.01–7.39 (m, 4H + 4H') | 4/1 |
| 13 | CH₃ | CH₃ | CH₃ | Propyl | Propyl | 3-Fluoro | N-propyl-N-[(4,5,6-trimethyl-7-oxo-3-propyl(4,7-dihydropyrazolo[1,5a]pyrimidin-2-yl))methyl](3- | 0.67 (t, 3H), 0.83 (br s, 3H'), 1.03 (t, 3H), 0.88 (t, 3H'), 1.47–1.67 (m, 4H + 4H'), 2.20 (s, 3H + 3H'), 2.40 (s, 3H + 3H'), 2.80 (t, 2H + 2H'), 3.20 (t, 2H), 3.42 (br | 4/1 |

TABLE 1-continued

| No. | R1 | R2 | R3 | R4 | R5 | X | Name | ¹H NMR (CDCl₃) δ | H/H' |
|---|---|---|---|---|---|---|---|---|---|
| | | | | | | | fluorophenyl)carboxamide | s, 2H'), 3.81 (s, 3H), 3.72 (s, 3H'), 4.95 (s, 2H), 4.65 (s, 2H'), 7.03–7.43 (m, 4H + 4H') | |
| 14 | H | CH₃ | H | Ethyl | isobutyl | 3-Chloro | N-[(3-ethyl-5-methyl-7-oxo(4,7-dihydropyrazolo[1,5a]pyrimidin-2-yl))methyl]-N-(2-methylpropyl)(3-chlorophenyl)carboxamide | 0.67 (d, 6H), 0.80–0.94 (m, 6H' + 3H'), 1.05 (t, 3H), 2.00 (m 1H + 1H'), 2.25 (s, 3H + 3H'), 2.55 (q, 2H), 2.33 (br s, 2H'), 3.09 (d, 2H), 3.20 (d, 2H'), 4.84 (s, 2H), 4.55 (s, 2H'), 5.59 (s, 1H), 5.62 (s, 1H'), 7.20–7.40 (m, 4H + 4H') | 3/1 |
| 15 | H | CH₃ | CH₃ | Ethyl | isobutyl | 3-Chloro | N-[(3-ethyl-4,5-dimethyl-7-oxo(4,7-dihydropyrazolo[1,5a]pyrimidin-2-yl))methyl]-N-(2-methylpropyl)(3-chlorophenyl)carboxamide | 0.72 (d, 6H), 0.93 (d, 6H'), 1.25 (s, 3H), 1.05 (t, 3H'), 2.20 (m, 1H + 1H'), 2.38 (s, 3H + 3H'), 2.87 (q, 2H), 2.49 (q, 2H'), 3.10 (d, 2H), 3.25 (d, 2H'), 3.84 (s, 3H), 3.72 (s, 3H'), 4.94 (s, 2H), 4.65 (s, 2H'), 5.73 (s, 1H + 1H'), 7.23–7.50 (m, 4H + 4H') | 3/1 |
| 16 | H | CH₃ | CH₃— | Propyl | secbutyl | 3-Chloro | N-[(4,5-dimethyl-7-oxo-3-propyl(4,7-dihydropyrazolo[1,5a]pyrimidin-2-yl))methyl]-N-(methylpropyl)(3-chlorophenyl)carboxamide | 0.75 (t, 3H), 1.01 (t, 3H), 1.15 (d, 3H), 1.40–1.85 (m, 4H), 2.34 (s, 3H), 2.85 (t, 2H), 3.64–3.80 (m, 4H), 4.54 (d, 1H), 5.09 (d, 1H), 5.70 (s, 1H), 7.20–7.46 (m, 4H) | |
| 17 | H | CH₃ | CH₃ | Propyl | (CH₃CH₂)₂CH— | 3-Chloro | N-[(4,5-dimethyl-7-oxo-3-propyl(4,7-dihydropyrazolo[1,5a]pyrimidin-2-yl))methyl]-N-(ethylpropyl)(3-chlorophenyl)carboxamide | 0.77 (t, 6H), 0.88 (t, 6H'), 1.02 (t, 3H + 3H'), 1.40–1.80 (m, 6H + 6H'), 2.35 (s, 3H + 3H'), 2.88 (t, 2H), 2.43 (t, 2H'), 3.47 (m, 1H + 1H'), 3.78 (s, 3H), 3.68 (s, 3H'), 4.80 (s, 2H), 4.51 (s, 2H'), 5.69 (s, 1H + 1H'), 7.25–7.48 (m, 4H + 4H') | 5/1 |
| 18 | H | CH₃ | CH₃ | Propyl | benzyl | 3-Chloro | N-[(4,5-dimethyl-7-oxo-3-propyl(4,7-dihydropyrazolo[1,5a]pyrimidin-2-yl))methyl]-N-benzyl(3-chlorophenyl)carboxamide | 1.00 (t, 3H), 0.73 (br s, 3H'), 1.58 (m, 2H), 1.23 (m, 2H'), 2.36 (s, 3H + 3H'), 2.80 (t, 2H), 2.24 (br s, 2H'), 3.76 (s, 3H), 3.62 (s, 3H'), 4.67 (s, 2H), 4.49 (s, 2H'), 4.84 (s, 2H + 2H'), 5.72 (s, 1H + 1H'), 7.10–7.54 (m, 9H + 9H') | 3/1 |
| 19 | CH₃ | CH₃ | H | Propyl | Propyl | 3-Chloro | N-[(5,6-dimethyl-7-oxo-3-propyl(4,7-dihydropyrazolo[1,5a]pyrimidin-2-yl))methyl]-N-propyl(3-chlorophenyl)carboxamide | 0.63–0.92 (m, 6H + 6H'), 1.40–1.60 (m, 4H + 4H'), 2.03 (s, 3H + 3H'), 2.23–2.55 (m, 5H + 5H'), 3.21 (m, 2H + 2H'), 4.76 (s, 2H), 4.52 (s, 2H'), 7.20–7.40 (m, 4H + 4H') | 3/1 |
| 20 | CH₃ | CH₃ | CH₃ | Propyl | Propyl | 3-Chloro | N-propyl-N-[(4,5,6-trimethyl-7-oxo-3-propyl(4,7-dihydropyrazolo[1,5a]pyrimidin-2-yl))methyl](3-chlorophenyl)carboxamide | 0.68 (t, 3H), 0.83 (t, 3H'), 1.03 (t, 3H), 0.90 (t, 3H'), 1.40–1.63 (m, 4H + 4H'), 2.20 (s, 3H + 3H'), 2.41 (s, 3H + 3H'), 2.80 (t, 2H + 2H'), 3.20 (t, 2H + 2H'), 3.81 (s, 3H), 3.74 (s, 3H'), 4.96 (s, 2H), 4.61 (s, 3H'), 7.20–7.40 (m, 4H + 4H') | 4/1 |
| 21 | H | CH₃ | H | Propyl | isobutyl | 2,5-Difluoro | N-[(5-methyl-7-oxo-3-propyl(4,7-dihydropyrazolo[1,5a]pyrimidin-2-yl))methyl]-N-(2-methylpropyl) (2,5-difluorophenyl)carboxamide | 0.60–0.85 (m, 9H + 9H'), 1.49 (m, 2H + 2H'), 1.97 (m, 1H + 1H'), 2.04–2.60 (m, 5H + 5H'), 2.96 (d, 2H + 2H'), 4.83 (s, 2H), 4.50 (s, 2H'), 5.60 (s, 1H + 1H'), 6.97–7.08 (m, 3H + 3H') | 2/1 |
| 22 | H | CH₃ | CH₃ | Propyl | isobutyl | 2,5-Difluoro | N-[(4,5-dimethyl-7-oxo-3-propyl(4,7-dihydropyrazolo[1,5a]pyrimidin-2-yl))methyl]-N-(2-methylpropyl) (2,5-difluorophenyl)carboxamide | 0.68 (d, 6H), 0.92 (d, 6H'), 1.02 (t, 3H), 0.85 (t, 3H'), 1.50 (m, 2H + 2H'), 2.21 (m, 1H + 1H'), 2.40 (s, 3H), 2.35 (s, 3H'), 2.76 (t, 2H), 2.43 (t, 2H'), 2.98 (d, 2H + 2H'), 3.81 (s, 3H), 3.72 (s, 3H'), 4.97 (s, 2H), 4.60 (s, 2H'), 5.73 (s, 1H + 1H'), 7.00–7.23 (m, 3H + 3H') | 3/1 |

TABLE 1-continued

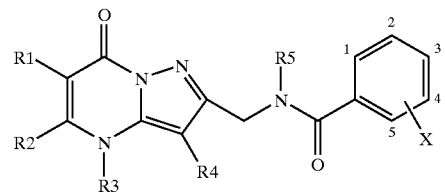

| No. | R1 | R2 | R3 | R4 | R5 | X | Name | $^1$H NMR (CDCl$_3$) δ | H/H' |
|---|---|---|---|---|---|---|---|---|---|
| 23 | H | CH$_3$ | H | Ethyl | Ethyl | 2,5-Difluoro | N-ethyl-N-[(3-ethyl-5-methyl-7-oxo(4,7-dihydropyrazolo[1,5a]pyrimidin-2-yl))methyl](2,5-difluorophenyl)carboxamide | 0.83–1.13 (m, 6H + 6H'), 2.36 (s, 3H), 2.32 (s, 3H'), 2.57 (q, 2H + 2H'), 3.20 (q, 2H + 2H'), 4.87 (s, 2H), 4.52 (s, 2H'), 5.62 (s, 1H + 1H'), 6.93–7.11 (m, 3H + 3H') | 3/1 |
| 24 | H | CH$_3$ | CH$_3$ | Ethyl | isobutyl | 2,5-Difluoro | N-[(3-ethyl-4,5-dimethyl-7-oxo(4,7-dihydropyrazolo[1,5a]pyrimidin-2-yl))methyl]-N-(2-methylpropyl) (2,5-difluorophenyl)carboxamide | 0.68 (d, 6H), 0.91 (d, 6H'), 1.24 (t, 3H), 1.05 (t, 3H'), 2.20 (m, 1H + 1H'), 2.37 (s, 3H), 2.34 (s, 3H'), 2.83 (q, 2H), 2.50 (q, 2H'), 2.96 (d, 2H), 3.12 (m, 2H'), 3.80 (s, 3H), 3.74 (s, 3H'), 4.96 (s, 2H), 4.60 (s, 2H'), 5.71 (s, 1H), 5.69 (s, 1H'), 6.75–7.00 (m, 2H + 2H'), 7.33–7.47 (m, 1H + 1H') | 3/1 |
| 25 | H | CH$_3$ | CH$_3$ | Propyl | secbutyl | 2,5-Difluoro | N-[(4,5-dimethyl-7-oxo-3-propyl(4,7-dihydropyrazolo[1,5a]pyrimidin-2-yl))methyl]-N-(methylpropyl) (2,5-difluorophenyl)carboxamide | 0.75 (t, 3H), 0.80 (t, 3H'), 1.04 (t, 3H), 0.91 (t, 3H'), 1.09 (d, 3H), 1.18 (d, 3H'), 1.40–1.69 (m, 4H + 4H'), 2.38 (s, 3H), 2.36 (s, 3H'), 2.85 (t, 2H), 2.45 (t, 2H'), 3.60 (m, 1H + 1H'), 3.80 (s, 3H), 3.70 (s, 3H'), 4.65 (d, 1H + 1H'), 5.20 (br s, 1H + 1H'), 5.70 (s, 1H), 5.73 (s, 1H'), 7.01–7.25 (m, 3H + 3H') | 4/1 |
| 26 | H | CH$_3$ | CH$_3$ | Propyl | (CH$_3$CH$_2$)$_2$CH— | 2,5-Difluoro | N-[(4,5-dimethyl-7-oxo-3-propyl(4,7-dihydropyrazolo[1,5a]pyrimidin-2-yl))methyl]-N-(ethylpropyl) (2,5-difluorophenyl)carboxamide | 0.72 (t, 6H), 0.88 (br s, 6H'), 1.03 (t, 3H + 3H'), 1.40–1.80 (m, 6H + 6H'), 2.37 (s, 3H), 2.34 (s, 3H'), 2.83 (t, 2H), 2.45 (t, 2H'), 3.28 (m, 1H + 1H'), 3.80 (s, 3H), 3.68 (s, 3H'), 4.9 (br d, 2H), 4.48 (s, 2H'), 5.71 (s, 1H + 1H'), 7.00–7.33 (m, 3H + 3H') | 5/1 |
| 27 | H | CH$_3$ | CH$_3$ | Propyl | benzyl | 2,5-Difluoro | N-[(4,5-dimethyl-7-oxo-3-propyl(4,7-dihydropyrazolo[1,5a]pyrimidin-2-yl))methyl]-N-benzyl(2,5-difluorophenyl)carboxamide | 1.02 (t, 3H), 0.71 (t, 3H'), 1.58 (m, 2H), 1.25 (m, 2H'), 2.38 (s, 3H), 2.35 (s, 3H'), 2.80 (t, 2H), 2.24 (t, 2H'), 3.78 (s, 3H), 3.60 (s, 3H'), 4.55 (s, 2H), 4.49 (s, 2H'), 4.89 (s, 2H + 2H'), 5.74 (s, 1H + 1H'), 7.00–7.28 (m, 8H + 8H') | 3/1 |
| 28 | CH$_3$ | CH$_3$ | H | Propyl | Propyl | 2,5-Difluoro | N-[(5,6-dimethyl-7-oxo-3-propyl (4,7-dihydropyrazolo[1,5a]pyrimidin-2-yl))methyl]-N-propyl(2,5-difluorophenyl)carboxamide | 0.52–0.97 (m, 6H + 6H'), 1.33–1.60 (m, 4H + 4H'), 2.07 (s, 3H + 3H'), 2.20–2.60 (m, 5H + 5H'), 3.20 (m, 2H + 2H'), 4.84 (s, 2H), 4.46 (s, 2H'), 6.87–7.10 (br s 3H + 3H') | 3/1 |
| 29 | CH$_3$ | CH$_3$ | CH$_3$— | Propyl | Propyl | 2,5-Difluoro | N-propyl-N-[(4,5,6-trimethyl-7-oxo-3-propyl(4,7-dihydropyrazolo[1,5a]pyrimidin-2-yl))methyl](2,5-difluorophenyl)carboxamide | 0.64 (t, 3H), 0.85 (t, 3H'), 1.05 (t, 3H), 0.90 (t, 3H'), 1.30–1.68 (m, 4H + 4H'), 2.20 (s, 3H), 2.16 (s, 3H'), 2.40 (s, 3H), 2.36 (s, 3H'), 2.76 (t, 2H), 2.44 (t, 2H'), 3.10 (t, 2H + 2H'), 3.82 (s, 3H), 3.73 (t, 3H'), 4.96 (s, 2H), 4.60 (s, 2H'), 7.00–7.24 (m, 3H + 3H') | 3/1 |

TABLE 2

| No. | R1 | R2 | R3 | R4 | R5 | X | Name | $^1$H NMR (CDCl3) δ |
|---|---|---|---|---|---|---|---|---|
| 30 | H | CH$_3$ | CH$_3$ | Propyl | isoButyl | 3-Fluoro | N-[(7-methoxy-5-methyl-3-propyl(pyrazolo[1,5-a]pyrimidin-2-yl))methyl]-N-(2-methylpropyl)(3-fluorophenyl)carboxamide | 0.75 (d, 6H), 1.00 (t, 3H), 1.70 (m, 2H), 1.89 (m, 1H), 2.36 (s, 3H), 2.62 (t, 2H), 3.05 (d, 2H), 4.07 (s, 3H), 4.93 (s, 2H), 5.98 (s, 1H), 7.07–7.45 (m, 4H) |
| 31 | H | CH$_3$ | CH$_3$ | Propyl | Propyl | 3-Fluoro | N-[(7-methoxy-5-methyl-3-propyl(pyrazolo[1,5-a]pyrimidin-2-yl))methyl]-N-propyl(3-fluorophenyl)carboxamide | 0.73 (t, 3H), 1.00 (t, 3H), 1.49 (m, 2H), 1.69 (m, 2H), 2.36 (s, 3H), 2.64 (t, 2H), 3.11 (t, 2H), 4.09 (s, 3H), 4.93 (s, 2H), 5.94 (s, 1H), 7.07–7.47 (m, 4H) |
| 32 | H | CH$_3$ | CH$_3$ | Ethyl | isoButyl | 3-Fluoro | N-[(3-ethyl-7-methoxy-5-methyl(pyrazolo[1,5-a]pyrimidin-2-yl))methyl]-N-(2-methylpropyl)(3-fluorophenyl)carboxamide | 0.74 (d, 6H), 1.27 (t, 3H), 1.89 (m, 1H), 2.36 (s, 3H), 2.69 (q, 2H), 3.07 (d, 2H), 4.07 (s, 3H), 4.91 (s, 2H), 5.98 (s, 1H0, 7.05–7.47 (m, 4H) |
| 33 | H | CH$_3$ | CH$_3$ | Ethyl | isoButyl | 3-Chloro | N-[(3-ethyl-7-methoxy-5-methyl(pyrazolo[1,5-a]pyrimidin-2-yl))methyl]-N-(2-methylpropyl)(3-chlorophenyl)carboxamide | 0.75 (d, 6H), 1.29 (t, 3H), 1.89 (m, 1H), 2.36 (s, 3H), 2.69 (q, 2H), 3.05 (d, 2H), 4.08 (s, 3H), 4.92 (s, 2H), 5.98 (s, 1H), 7.25–7.45 (m, 4H) |
| 34 | H | CH$_3$ | CH$_3$ | Propyl | isoButyl | 2,5-di-fluoro | N-[(7-methoxy-5-methyl-3-propyl(pyrazolo[1,5-a]pyrimidin-2-yl))methyl]-N-(2-methylpropyl)(2,5-difluorophenyl)carboxamide | 0.76 (d, 6H), 0.98 (t, 3H), 1.70 (m, 2H), 1.85 (m, 1H), 2.36 (s, 3H), 2.62 (t, 2H), 2.95 (d, 2H), 4.09 (s, 3H), 4.98 (br s, 2H), 5.96 (s, 1H), 7.04–7.20 (m, 3H) |
| 35 | H | CH$_3$ | CH$_3$ | Ethyl | isoButyl | 2,5-di-fluoro | N-[(3-ethyl-7-methoxy-5-methyl(pyrazolo[1,5-a]pyrimldin-2-yl))methyl]-N-(2-methylpropyl)(2,5-difluorophenyl)carboxamide | 0.73 (d, 6H), 1.27 (t, 3H), 1.87 (m, 1H), 2.36 (s, 3H), 2.69 (q, 2H), 2.95 (d, 2H), 4.09 (s, 3H), 4.96 (br s, 2H), 5.96 (s, 1H), 6.84–7.02 (m, 2H), 7.40 (m, 1H) |

TABLE III

| No. | R3 | R4 | R5 | X | Name | $^1$H NMR (CDCl3) δ | H/H' |
|---|---|---|---|---|---|---|---|
| 36 | H | Propyl | Propyl | 3-Fluoro | N-[(8-oxo-3-propyl(4,5,6,7,8a-pentahydrocyclopenta[2,1-d]pyrazolo[1,5a]pyrimidin-2-yl))methyl]-N-propyl(3-fluorophenyl)carboxamide | 0.64 (br s, 3H + 3H'), 0.98 (br s, 3H + 3H'), 1.40–1.60 (br s, 4H + 4H'), 2.09 (br s, 2H + 2H'), 2.50 (br s, 2H), 2.27 (br s, 2H'), 2.69–2.95 (m, 4H + 4H'), 3.14 (br s, 2H), 3.30 (br s, 2H'), 4.80 (s, 2H), 4.54 (s, 2H'), 7.01–7.38 (m, 4H + 4H') | 3/1 |
| 37 | CH$_3$ | Propyl | Propyl | 3-fluoro | N-[(4-methyl-8-oxo-3-propyl(4,5,6,7,8a-pentahydrocyclopenta[2,1-d]pyrazolo[1,5a]pyrimidin-2-yl))methyl]-N-propyl(3-fluorophenyl)carboxamide | 0.69 (t, 3H), 0.84 (br s, 3H'), 1.02 (t, 3H), 0.90 (br s, 3H'), 1.47–1.67 (m, 4H + 4H'), 2.16 (m, 2H + 2H'), 2.80 (t, 2H), 2.41 (br s, 2H'), 3.00 (t, 2H + 2H'), 2.93 (t, 2H + 2H'), 3.20 (t, 2H), 3.42 (br s, 2H'), 3.80 (s, 3H), 3.73 (s, 3H'), 4.95 (s, 2H), 4.64 (s, 2H'), 7.04–7.40 (m, 4H + 4H') | 3/1 |
| 38 | H | Ethyl | Propyl | 3-fluoro | N-[(3-ethyl-8-oxo(4,5,6,7,8a-pentahydrocyclopenta[2,1-d]pyrazolo[1,5a]pyrimidin-2-yl))methyl]-N-propyl(3- | 0.63 (br s, 3H), 0.83 (br s, 3H'), 1.05 (br s, 3H), 0.90 (br s, 3H'), 1.50 (br s, 2H + 2H'), 2.11 (br s, 2H + 2H'), 2.56 (br s, 2H), 2.31 (br s, 2H'), | 3/1 |

TABLE III-continued

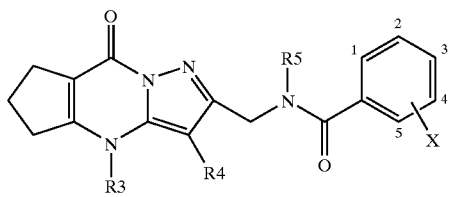

| No. | R3 | R4 | R5 | X | Name | $^1$H NMR (CDCl3) δ | H/H' |
|---|---|---|---|---|---|---|---|
| | | | | | fluorophenyl)carboxamide | 2.70–3.00 (m, 4H + 4H'), 3.20 (br s, 2H), 3.32 (br s, 2H'), 4.83 (s, 2H), 4.55 (s, 2H'), 7.02–7.39 (m, 4H + 4H') | |
| 39 | CH$_3$ | Ethyl | Propyl | 3-fluoro | N-[(3-ethyl-4-methyl-8-oxo(4,5,6,7,8a-pentahydrocyclopenta[2,1-d]pyrazolo[1,5a]pyrimidin-2-yl))methyl]-N-propyl(3-fluorophenyl)carboxamide | 0.67 (t, 3H), 0.89 (br s, 3H'), 1.23 (t, 3H), 1.05 (br s, 3H'), 1.60 (m, 2H + 2H'), 2.16 (m, 2H + 2H'), 2.85 (q, 2H), 2.50 (br s, 2H'), 2.96 (t, 2H + 2H'), 3.02 (t, 2H + 2H'), 3.20 (t, 2H), 3.40 (br s, 2H'), 3.82 (s, 3H), 3.72 (s, 3H'), 4.96 (s, 2H), 4.65 (s, 2H'), 7.05–7.44 (m, 4H + 4H') | 3/1 |
| 40 | H | Ethyl | Propyl | 3-Chloro | N-[(3-ethyl-8-oxo(4,5,6,7,8a-pentahydrocyclopenta[2,1-d]pyrazolo[1,5a]pyrimidin-2-yl))methyl]-N-propyl(3-chlorophenyl)carboxamide | 0.65 (br s, 3H), 0.84 (br s, 3H'), 1.16 (br s, 3H), 0.91 (br s, 3H'), 1.50 (br s, 2H + 2H'), 2.11 (br s, 2H + 2H'), 2.54 (br s, 2H), 2.30 (br s, 2H'), 2.75–2.94 (m, 4H + 4H'), 3.20 (br s, 2H), 3.34 (br s, 2H'), 4.84 (s, 2H), 4.56 (s, 2H'), 7.24–7.53 (m, 4H + 4H') | 4/1 |
| 41 | CH$_3$ | Ethyl | Propyl | 3-Chloro | N-[(3-ethyl-4-methyl-8-oxo(4,5,6,7,8a-pentahydrocyclopenta[2,1-d]pyrazolo[1,5a]pyrimidin-2-yl))methyl]-N-propyl(3-chlorophenyl)carboxamide | 0.69 (t, 3H), 0.90 (br s, 3H'), 1.24 (t, 3H), 1.04 (br s, 3H'), 1.60 (m, 2H + 2H'), 2.19 (m, 2H + 2H'), 2.85 (q, 2H), 2.50 (br s, 2H'), 2.96 (t, 2H + 2H'), 3.01 (t, 2H + 2H'), 3.20 (t, 2H), 3.40 (br s, 2H'), 3.83 (s, 3H), 3.77 (s, 3H'), 4.95 (s, 2H), 4.63 (s, 2H'), 7.20–7.48 (m, 4H + 4H') | 3/1 |
| 42 | H | Ethyl | Propyl | 2,5-difluoro | N-[(3-ethyl-8-oxo(4,5,6,7,8a-pentahydrocyclopenta[2,1-d]pyrazolo[1,5a]pyrimidin-2-yl))methyl]-N-propyl(2,5-difluorophenyl)carboxamic | 060–1.13 (m, 6H + 6H'), 1.50 (m, 2H + 2H'), 2.10 (br s, 2H + 2H'), 2.60 (br s, 2H + 2H'), 2.75–2.95 (m, 4H + 4H'), 3.08 (br s, 2H), 3.28 (q, 2H'), 4.87 (s, 2H), 4.52 (s, 2H'), 6.93–7.13 (br s, 3H + 3H') | 3/1 |
| 43 | CH$_3$ | Ethyl | Propyl | 2,5-difluoro | N-[(3-ethyl-4-methyl-8-oxo(4,5,6,7,8a-pentahydrocyclopenta[2,1-d]pyrazolo[1,5a]pyrimidin-2-yl))methyl]-N-propyl(2,5-difluorophenyl)carboxamide | 0.68 (t, 3H), 0.88 (t, 3H'), 1.23 (t, 3H), 1.03 (t, 3H'), 1.54 (m, 2H), 1.65 (m, 2H'), 2.18 (m, 2H + 2H'), 2.85 (q, 2H), 2.51 (q, 2H'), 2.95 (m, 2H + 2H'), 3.00 (t, 2H + 2H'), 3.13 (t, 2H + 2H'), 3.83 (s, 3H), 3.75 (s, 3H'), 5.00 (s, 2H), 4.60 (s, 2H'), 7.02–7.23 (m, 3H + 3H') | 4/1 |

Example 5

Ligand Binding Assay

The affinity of compounds of this invention for the benzodiazepine site of the GABA$_A$ receptor is demonstrated using a binding assay essentially described by Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contained 100 μl of tissue homogenate, 100 μl of radioligand, (0.5 nM $^3$H-Ro15-1788 [$^3$H-Flumazenil], specific activity 80 Ci/mmol), and test compound or control (see below), and are brought to a total volume of 500 μl with Buffer A. Incubations are maintained for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 μM Diazepam (Research Biochemicals International, Natick, Mass.). Data are collected in triplicate, averaged, and percent inhibition of total specific binding (Total Specific Binding=Total−Nonspecific) is calculated for each compound.

A competition binding curve is generated with up to 11 points spanning the compound concentration range from $10^{-12}$M to $10^{-5}$M obtained per curve by the method described above for determining percent inhibition. K$_i$ values are calculated according to the Cheng-Prussof equation.

Each of the compounds of the above examples has a $K_i$ of <1 µM in this assay. Preferred compounds of the invention exhibit $K_i$ values of less than 100 nM and more preferred compounds of the invention exhibit $K_i$ values of less than 10 nM.

Example 6

Electrophysiology

The following assay is used to determine if a compound of the invention acts as an agonist, an antagonist, or an inverse agonist at the benzodiazepine site of the $GABA_A$ receptor.

Assays are carried out essentially as described in White and Gurley (NeuroReport 6:1313–1316, 1995) and White, Gurley, Hartnett, Stirling, and Gregory (Receptors and Channels 3:1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evocable GABA current (e.g., 1 µM–9 µM). Each oocyte is exposed to increasing concentrations of a compound being evaluated (test compound) in order to evaluate a concentration/effect relationship. Test compound efficacy is calculated as a percent-change in current amplitude: 100((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 µM RO15–1788, followed by exposure to GABA+1 µM RO15–1788+test compound. Percent change due to addition of compound is calculated as described above. Any percent change observed in the presence of RO15–1788 is subtracted from the percent changes in current amplitude observed in the absence of 1 µM RO15–1788. These net values are used for the calculation of average efficacy and $EC_{50}$ values by standard methods. To evaluate average efficacy and $EC_{50}$ values, the concentration/effect data are averaged across cells and fit to the logistic equation.

Example 7

MDCK Cytotoxicity Assay

This Example illustrates the evaluation of compound toxicity using a Madin Darby canine kidney (MDCK) cell cytoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog #30–2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOP-COUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When

What is claimed is:

1. A compound of the formula

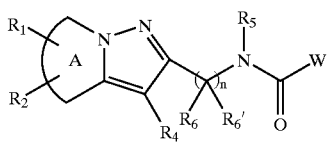

or a pharmaceutically acceptable salt thereof, wherein
n is 1, 2, or 3;

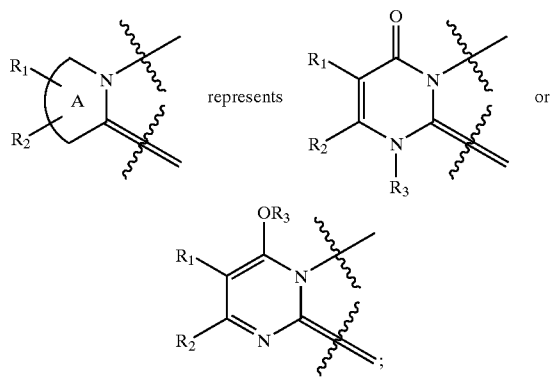

$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; or $R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy;

$R_3$, $R_4$ and $R_5$ are independently chosen from hydrogen; $C_1$–$C_6$ acyl; and $C_1$–$C_6$ alkyl; wherein each $C_1$–$C_6$ acyl and $C_1$–$C_6$ alkyl is optionally substituted with up to three substituents independently chosen from halogen, hydroxy, halo($C_1$–$C_2$)alkyl, halo ($C_1$–$C_2$)alkoxy, methoxy, ethoxy, $C_3$–$C_7$ cycloalkyl, phenyl, pyridyl, and pyrimidyl, wherein each of phenyl, pyridyl, and pyrimidyl is optionally substituted with up to three groups independently selected from halogen, $C_1$–$C_6$ alkyl, $C_1$–$C_6$ alkoxy, hydroxy and amino;

$R_6$ and $R_6'$ are independently selected at each occurrence from hydrogen and $C_1$–$C_6$ alkyl;

W is aryl or heteroaryl, each of which is optionally substituted with up to 5 groups independently selected from hydrogen, halogen, hydroxy, amino, mono- or di($C_1$–$C_6$)alkyl amino, halo ($C_1$–$C_6$)alkyl, halo ($C_1$–$C_6$)alkoxy, $C_1$–$C_6$ alkyl, and $C_1$–$C_6$ alkoxy.

2. A compound according to claim 1, wherein

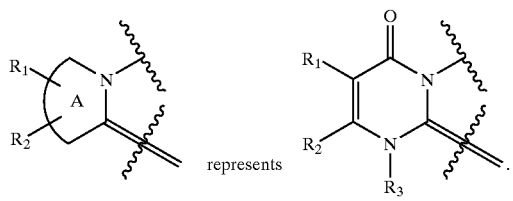

3. A compound according to claim 2, wherein W is optionally substituted heteroaryl.

4. A compound according to claim 3, wherein W is pyridyl, pyrimidinyl, pyridizinyl, pyrrolyl, imidazolyl, pyrazolyl or thiophenyl, each of which is optionally substituted with up to 5 groups independently selected from hydrogen, halogen, hydroxy, amino, mono- or di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy.

5. A compound according to claim 2, wherein W is optionally substituted aryl.

6. A compound according to claim 5, wherein W is phenyl optionally substituted with up to 5 groups independently selected from hydrogen, halogen, hydroxy, amino, mono- or di($C_1$–$C_6$)alkyl amino, halo($C_1$–$C_6$)alkyl, halo($C_1$–$C_6$) alkoxy, $C_1$–$C_6$ alkyl, and $C_1$–$C_6$ alkoxy.

7. A compound according to claim 6, wherein $R_4$ and $R_5$ are independently $C_1$–$C_6$ alkyl optionally substituted with 1 or 2 substituents independently chosen from halogen, hydroxy, trifluoromethyl, trifluoromethoxy, methoxy, ethoxy, $C_3$–$C_7$ cycloalkyl, phenyl, pyridyl, and pyrimidyl, wherein each of phenyl, pyridyl, and pyrimidyl is optionally substituted with up to three groups independently selected from halogen, $C_1$–$C_6$ alkyl, $C_1$–$C_6$ alkoxy, hydroxy and amino.

8. A compound according to claim 6, wherein $R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; and $R_3$, $R_4$ and $R_5$ are independently $C_1$–$C_6$ alkyl.

9. A compound according to claim 6, wherein $R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; and $R_3$, $R_4$ and $R_5$ are independently H or $C_1$–$C_6$ alkyl.

10. A compound according to claim 9, wherein $R_1$ and $R_2$ together with the atoms with which they are attached form a cyclopentenyl, cyclopentadienyl, cyclohexenyl, cyclohexadienyl, cycloheptatrienyl, cycloheptadienyl, phenyl, cyclooctadienyl, and cyclooctenyl, wherein each ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy; and $R_3$, $R_4$ and $R_5$ are independently $C_1$–$C_4$ alkyl.

11. A compound of the formula:

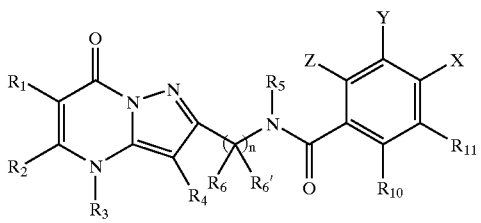

or a pharmaceutically acceptable salt thereof, wherein:
n is 1, 2, or 3;
$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy; or
$R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy;
$R_3$, $R_4$ and $R_5$ are independently chosen from (i) hydrogen; and (ii) $C_1$–$C_6$ acyl and $C_1$–$C_6$ alkyl, optionally substituted with up to three substituents independently chosen from halogen, hydroxy, halo($C_1$–$C_2$)alkyl, halo($C_1$–$C_2$)alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;
$R_6$ and $R_6'$ are independently selected at each occurrence from hydrogen and $C_1$–$C_6$ alkyl; and
$R_{10}$, $R_{11}$, X, Y and Z are independently selected from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy.

12. A compound of the formula:

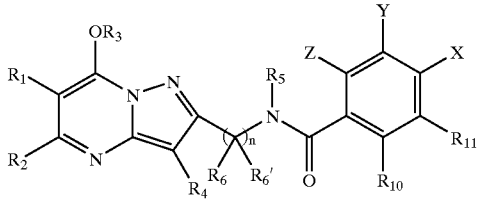

or a pharmaceutically acceptable salt thereof, wherein:
n is 1, 2, or 3;
$R_1$ and $R_2$ are independently chosen from hydrogen, halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl, and $C_1$–$C_6$ alkoxy, or
$R_1$ and $R_2$ together with the atoms with which they are attached form a partially saturated or unsaturated carbocyclic ring of from 3 to 8 carbon atoms, wherein the ring is optionally substituted by up to 5 substituents independently chosen from halogen, hydroxy, amino, mono- and di($C_1$–$C_6$)alkyl amino, halo($C_1$–$C_6$)alkyl, halo($C_1$–$C_6$)alkoxy, $C_1$–$C_6$ alkyl and $C_1$–$C_6$ alkoxy;
$R_3$, $R_4$ and $R_5$ are independently chosen from (i) hydrogen; and (ii) $C_1$–$C_6$ acyl and $C_1$–$C_6$ alkyl, optionally substituted with up to three substituents independently chosen from halogen, hydroxy, halo($C_1$–$C_2$)alkyl, halo($C_1$–$C_2$)alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;
$R_6$ and $R_6'$ are independently selected at each occurrence from hydrogen and $C_1$–$C_6$ alkyl; and
$R_{10}$, $R_{11}$, X, Y and Z are independently selected from hydrogen, halogen, hydroxy, amino, mono- and di($C_1$–$C_6$)alkyl amino, halo($C_1$–$C_6$)alkyl, halo($C_1$–$C_6$) alkoxy, $C_1$–$C_6$ alkyl and $C_1$–$C_6$ alkoxy.

13. A compound according to claim 6 of the formula:

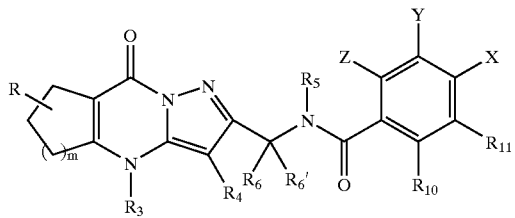

or a pharmaceutically acceptable salt thereof, wherein:
m is 1, 2, or 3;
R represents up to 5 groups independently chosen from hydrogen, halogen, hydroxy, amino, halo($C_1$–$C_6$)alkyl, halo($C_1$–$C_6$)alkoxy, $C_1$–$C_6$ alkyl, and $C_1$–$C_6$ alkoxy;
$R_3$, $R_4$ and $R_5$ are independently chosen from (i) hydrogen; and (ii) $C_1$–$C_6$ acyl and $C_1$–$C_6$ alkyl, optionally substituted with up to three substituents independently chosen from halogen, hydroxy, halo($C_1$–$C_2$)alkyl, halo($C_1$–$C_2$)alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;
$R_6$ and $R_6'$ are independently chosen from hydrogen, methyl, and ethyl; and
$R_{10}$, $R_{11}$, X, Y and Z are independently selected from hydrogen, halogen, hydroxy, amino, halo($C_1$–$C_6$)alkyl, halo($C_1$–$C_6$)alkoxy, $C_1$–$C_6$ alkyl and $C_1$–$C_6$ alkoxy.

14. A compound according to claim 13 of the formula:

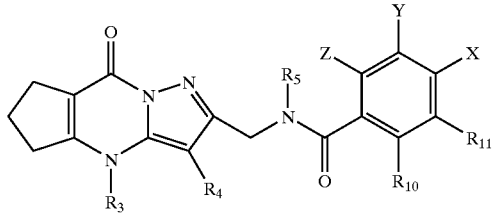

or a pharmaceutically acceptable salt thereof, wherein:
$R_3$, $R_4$ and $R_5$ are independently chosen from (i) hydrogen; and
(ii) $C_1$–$C_6$ acyl and $C_1$–$C_6$ alkyl, optionally substituted with up to three substituents independently chosen from halogen, hydroxy, halo($C_1$–$C_2$)alkyl, halo($C_1$–$C_2$) alkoxy, methoxy, ethoxy, $C_3$–$C_7$ cycloalkyl, phenyl, pyridyl and pyrimidyl, wherein each of phenyl, pyridyl and pyrimidyl is optionally substituted with up to three groups selected independently from halogen, $C_1$–$C_6$ alkyl, $C_1$–$C_6$ alkoxy, hydroxy and amino;

$R_{10}$, $R_{11}$, X, Y and Z are selected from hydrogen, halogen, hydroxy, amino, halo($C_1$–$C_6$)alkyl, halo($C_1$–$C_6$) alkoxy, $C_1$–$C_6$ alkyl and $C_1$–$C_6$ alkoxy.

15. A compound according to claim 14, wherein:

$R_3$ is hydrogen, methyl or ethyl;

$R_4$ and $R_5$ are independently $C_2$–$C_6$ alkyl; and $R_{10}$, $R_{11}$, X, W, Y and Z are independently hydrogen, halogen or methyl.

16. A compound according to claim 11, wherein:

n is 1; and $R_1$ and $R_2$ are independently chosen from hydrogen, halogen, hydroxy, amino, halo($C_1$–$C_6$) alkyl, halo ($C_1$–$C_6$) alkoxy, $C_1$–$C_6$ alkyl and $C_1$–$C_6$ alkoxy.

17. A compound according to claim 16, wherein:

$R_1$, $R_2$, and $R_3$ are independently chosen from hydrogen, methyl, and ethyl;

$R_4$ and $R_5$ are independently chosen from $C_2$–$C_6$ alkyl and benzyl;

$R_{10}$, $R_{11}$, X, Y and Z are independently selected from hydrogen, halogen and methyl; and $R_6$ and $R_6'$ are both hydrogen.

18. A compound according to claim 11, wherein n is 1.

19. A compound according to claim 18, wherein:

$R_1$ and $R_2$ are independently chosen from hydrogen, methyl and ethyl;

$R_3$ is methyl or ethyl;

$R_6$ and $R_6'$ are both hydrogen; and $R_{10}$, $R_{11}$, X, W, Y and Z are independently chosen from hydrogen, halogen, methyl, and methoxy.

20. A compound according to claim 1, which is N-[(5-methyl-7-oxo-3-propyl(4,7-dihydropyrazolo[1,5a]pyrimidin-2-yl)) methyl]-N-propyl(3-fluorophenyl) carboxamide.

21. A compound according to claim 1, which is N-[(4,5-dimethyl-7-oxo-3-propyl(4,7-dihydropyrazolo [1,5a]pyrimidin-2-yl))methyl]-N-propyl(3-fluorophenyl) carboxamide.

22. A compound according to claim 1, which is N-[(5-methyl-7-oxo-3-propyl(4,7-dihydropyrazolo[1,5a]pyrimidin-2-yl)) methyl]-N-(2-methylpropyl)(3-fluorophenyl)carboxamide.

23. A compound according to claim 1, which is N-[(4,5-dimethyl-7-oxo-3-propyl(4,7-dihydropyrazolo[1,5a]pyrimidin-2-yl)) methyl]-N-(2-methylpropyl)(3-fluorophenyl)carboxamide.

24. A compound according to claim 1, which is N-[(3-ethyl-4,5-dimethyl-7-oxo(4,7-dihydropyrazolo[1,5a]pyrimidin-2-yl)) methyl]-N-(2-methylpropyl)(3-fluorophenyl)carboxamide.

25. A compound according to claim 1, which is N-[(4-ethyl-5-methyl-7-oxo-3-propyl (4,7-dihydropyrazolo[1,5a]pyrimidin-2-yl))methyl]-N-propyl(3-fluorophenyl) carboxamide.

26. A compound according to claim 1, which is N-[(3-ethyl-5,6-dimethyl-7-oxo(4,7-dihydropyrazolo[1,5a]pyrimidin-2-yl))methyl]-N-propyl(3-fluorophenyl) carboxamide.

27. A compound according to claim 1, which is N-[(3-ethyl-4,5,6-trimethyl-7-oxo(4,7-dihydropyrazolo[1,5a]pyrimidin-2-yl))methyl]-N-propyl(3-fluorophenyl) carboxamide.

28. A compound according to claim 1, which is N-[(4,5-dimethyl-7-oxo-3-propyl(4,7-dihydropyrazolo[1,5a]pyrimidin-2-yl))methyl]-N-(methylpropyl)(3-fluorophenyl) carboxamide.

29. A compound according to claim 1, which is N-[(4,5-dimethyl-7-oxo-3-propyl(4,7a-dihydropyrazolo[1,5a]pyrimidin-2-yl))methyl]-N-(ethylpropyl)(3-fluorophenyl) carboxamide.

30. A compound according to claim 1, which is N-[(4,5-dimethyl-7-oxo-3-propyl(4,7a-dihydropyrazolo[1,5a]pyrimidin-2-yl))methyl]-N-benzyl(3-fluorophenyl) carboxamide.

31. A compound according to claim 1, which is N-[(5,6-dimethyl-7-oxo-3-propyl(4,7a-dihydropyrazolo[1,5a]pyrimidin-2-yl))methyl]-N-propyl(3-fluorophenyl) carboxamide.

32. A compound according to claim 1, which is N-propyl-N-[(4,5,6-trimethyl-7-oxo-3-propyl(4,7-dihydropyrazolo[1,5a]pyrimidin-2-yl))methyl](3-fluorophenyl) carboxamide.

33. A compound according to claim 1, which is N-[(3-ethyl-5-methyl-7-oxo(4,7-dihydropyrazolo [1,5a]pyrimidin-2-yl))methyl]-N-(2-methylpropyl) (3chlorophenyl) carboxamide.

34. A compound according to claim 1, which is N-[(3-ethyl-4,5-dimethyl-7-oxo (4,7-dihydropyrazolo[1,5a]pyrimidin-2-yl)methyl]-N-(2-methylpropyl)(3-chlorophenyl)carboxamide.

35. A compound according to claim 1, which is N-[(4,5-dimethyl-7-oxo-3-propyl(4,7-dihydropyrazolo [1,5a]pyrimidin-2-yl))methyl]-N-(methylpropyl)(3-chlorophenyl) carboxamide.

36. A compound according to claim 1, which is N-[(4,5-dimethyl-7-oxo-3-propyl(4,7-dihydropyrazolo [1,5a]pyrimidin-2-yl))methyl]-N-(ethylpropyl)(3-chlorophenyl) carboxamide.

37. A compound according to claim 1, which is N-[(4,5-dimethyl-7-oxo-3-propyl(4,7-dihydropyrazolo [1,5a]pyrimidin-2-yl))methyl]-N-benzyl(3-chlorophenyl) carboxamide.

38. A compound according to claim 1, which is N-[(5,6-dimethyl-7-oxo-3-propyl(4,7-dihydropyrazolo [1,5a]pyrimidin-2-yl))methyl]-N-propyl(3-chlorophenyl) carboxamide.

39. A compound according to claim 1, which is N-propyl-N-[(4,5,6-trimethyl-7-oxo-3-propyl(4,7-dihydropyrazolo [1,5a]pyrimidin-2-yl))methyl](3-chlorophenyl) carboxamide.

40. A compound according to claim 1, which is N-[(5-methyl-7-oxo-3-propyl(4,7-dihydropyrazolo [1,5a]pyrimidin-2-yl))methyl]-N-(2-methylpropyl)(2,5-difluorophenyl) carboxamide.

41. A compound according to claim 1, which is N-[(4,5-dimethyl-7-oxo-3-propyl(4,7-dihydropyrazolo [1,5a]pyrimidin-2-yl))methyl]-N-(2-methylpropyl)(2,5-difluorophenyl) carboxamide.

42. A compound according to claim 1, which is N-ethyl-N-[(3-ethyl-5-methyl-7-oxo(4,7-dihydropyrazolo [1,5a]pyrimidin-2-yl))methyl](2,5-difluorophenyl)carboxamide.

43. A compound according to claim 1, which is N-[(3-ethyl-4,5-dimethyl-7-oxo(4,7-dihydropyrazolo [1,5a]

pyrimidin-2-yl))methyl]-N-(2-methylpropyl)(2,5-difluorophenyl)carboxamide.

44. A compound according to claim 1, which is N-[(4,5-dimethyl-7-oxo-3-propyl(4,7-dihydropyrazolo [1,5a] pyrimidin-2-yl))methyl]-N-(methylpropyl)(2,5-difluorophenyl) carboxamide.

45. A compound according to claim 1, which is N-[(4,5-dimethyl-7-oxo-3-propyl(4,7-dihydropyrazolo [1,5a] pyrimidin-2-yl))methyl]-N-(ethylpropyl)(2,5-difluorophenyl)carboxamide.

46. A compound according to claim 1, which is N-[(4,5-dimethyl-7-oxo-3-propyl(4,7-dihydropyrazolo [1,5a] pyrimidin-2-yl))methyl]-N-benzyl(2,5-difluorophenyl) carboxamide.

47. A compound according to claim 1, which is N-[(5,6-dimethyl-7-oxo-3-propyl(4,7-dihydropyrazolo [1,5a] pyrimidin-2-yl))methyl]-N-propyl(2,5-difluorophenyl) carboxamide.

48. A compound according to claim 1, which is N-propyl-N-[(4,5,6-trimethyl-7-oxo-3-propyl(4,7-dihydropyrazolo [1,5a]pyrimidin-2-yl))methyl](2,5-difluorophenyl) carboxamide.

49. A compound according to claim 1, which is N-[(7-methoxy-5-methyl-3-propyl(pyrazolo[1,5-a]pyrimidin-2-yl)) methyl]-N-(2-methylpropyi)(3-fluorophenyl) carboxamide.

50. A compound according to claim 1, which is N-[(7-methoxy-5-methyl-3-propyl(pyrazolo[1,5-a]pyrimidin-2-yl)) methyl]-N-propyl(3-fluorophenyl)carboxamide.

51. A compound according to claim 1, which is N-[(3-ethyl-7-methoxy-5-methyl(pyrazolo[1,5-a]pyrimidin-2-yl)) methyl]-N-(2-methylpropyl)(3-fluorophenyl) carboxamide.

52. A compound according to claim 1, which is N-[(3-ethyl-7-methoxy-5-methyl(pyrazolo[1,5-a]pyrimidin-2-yl)) methyl]-N-(2-methylpropyl)(3-chlorophenyl) carboxamide.

53. A compound according to claim 1, which is N-[(7-methoxy-5-methyl-3-propyl(pyrazolo[1,5-a]pyrimidin-2-yl)) methyl]-N-(2-methylpropyl)(2,5-difluorophenyl) carboxamide.

54. A compound according to claim 1, which is N-[(3-ethyl-7-methoxy-5-methyl(pyrazolo[1,5-a]pyrimidin-2-yl)) methyl]-N-(2-methylpropyl)(2,5-difluorophenyl) carboxamide.

55. A compound according to claim 1, which is N-[(8-oxo-3-propyl(4,5,6,7,8a-pentahydrocyclopenta[2,1-d] pyrazolo[1,5a]pyrimidin-2-yl))methyl]-N-propyl(3-fluorophenyl) carboxamide.

56. A compound according to claim 1, which is N-[(4-methyl-8-oxo-3-propyl(4,5,6,7,8a-pentahydrocyclopenta[2,1-d]pyrazolo [1,5a]pyrimidin-2-yi))methyl]-N-propyl(3-fluorophenyl) carboxamide.

57. A compound according to claim 1, which is N-[(3-ethyl-8-oxo(4,5,6,7,8a-pentahydrocyclopenta[2,1-d] pyrazolo[1,5a]pyrimidin-2-yl))methyl]-N-propyl(3-fluorophenyl) carboxamide.

58. A compound according to claim 1, which is N-[(3-ethyl-4-methyl-8-oxo(4,5,6,7,8a-pentahydrocyclopenta[2,1-d]pyrazolo[1,5a]pyrimidin-2-yl))methyl]-N-propyl(3-fluorophenyl) carboxamide.

59. A compound according to claim 1, which is N-[(3-ethyl-8-oxo(4,5,6,7,8a-pentahydrocyclopenta[2,1-d] pyrazolo[1,5a]pyrimidin-2-yl))methyl]-N-propyl(3-chlorophenyl) carboxamide.

60. A compound according to claim 1, which is N-[(3-ethyl-4-methyl-8-oxo(4,5,6,7,8a-pentahydrocyclopenta[2,1-d]pyrazolo[1,5a]pyrimidin-2-yl))methyl]-N-propyl(3-chlorophenyl) carboxamide.

61. A compound according to claim 1, which is N-[(3-ethyl-8-oxo(4,5,6,7,8a-pentahydrocyclopenta[2,1-d] pyrazolo[1,5a]pyrimidin-2-yl))methyl]-N-propyl(2,5-difluorophenyl) carboxamide.

62. A compound according to claim 1, which is N-[(3-ethyl-4-methyl-8-oxo(4,5,6,7,8a-pentahydrocyclopenta[2,1-d]pyrazolo[1,5a]pyrimidin-2-yl))methyl]-N-propyl(2,5-difluorophenyl) carboxamide.

63. A pharmaceutical composition comprising a compound of claim 1 in combination with a physiologically acceptable carrier or excipient.

64. The pharmaceutical composition of claim 63 wherein the pharmaceutical composition is formulated as an injectable fluid, an aerosol, a cream, a gel, a pill, a capsule, a syrup, or a transdermal patch.

65. A packaged pharmaceutical composition comprising the pharmaceutical composition of claim 63 in a container and instructions for using the composition to treat a patient suffering from anxiety, depression, a sleep disorder, attention deficit disorder, or Alzheimer's dementia.

66. A compound according to claim 1 wherein in an assay of $GABA_A$ receptor binding with 305 nM $^3$H-Flumazenil of radiologand, the compound exhibits an $K_i$ of 1 micromolar or less.

67. A compound according to claim 1 wherein in an assay of rat cortical $GABA_A$ receptor binding with 0.5 nM $^3$H-Flumazenil as radioligand, the compound exhibits an $K_i$ of 100 nanomolar or less.

68. A compound according to claim 1 wherein in an assay of rat cortical $GABA_A$ receptor binding with 0.5 nM $^3$H-Flumazenil as radioligand, the compound exhibits an $K_i$ of 10 nanomolar or less.

* * * * *